United States Patent
Rose

(10) Patent No.: US 7,813,942 B2
(45) Date of Patent: Oct. 12, 2010

(54) AFTER-HOURS RADIOLOGY SYSTEM

(75) Inventor: Greg Rose, Bellaire, TX (US)

(73) Assignee: Rose Radiology, LLC, Littleton, CO (US)

( * ) Notice: Subject to any disclaimer, the term of this patent is extended or adjusted under 35 U.S.C. 154(b) by 1400 days.

(21) Appl. No.: 11/243,372

(22) Filed: Oct. 4, 2005

(65) Prior Publication Data

US 2007/0078679 A1 Apr. 5, 2007

(51) Int. Cl.
*G06Q 10/00* (2006.01)
*G06Q 50/00* (2006.01)
*A61B 5/00* (2006.01)
*G06F 19/00* (2006.01)

(52) U.S. Cl. ............................................... 705/3; 705/2
(58) Field of Classification Search ...................... 705/2, 705/3
See application file for complete search history.

(56) References Cited

U.S. PATENT DOCUMENTS

| | | | | |
|---|---|---|---|---|
| 5,506,984 A * | 4/1996 | Miller | ........................... | 707/10 |
| 5,581,460 A * | 12/1996 | Kotake et al. | ................... | 705/3 |
| 5,926,526 A * | 7/1999 | Rapaport et al. | ......... | 379/88.25 |
| 2002/0016718 A1 * | 2/2002 | Rothschild et al. | ............. | 705/2 |
| 2002/0019751 A1 | 2/2002 | Rothschild et al. | | |
| 2002/0046061 A1 | 4/2002 | Wright et al. | | |
| 2002/0133373 A1 | 9/2002 | Silva-Craig et al. | | |
| 2002/0184055 A1 | 12/2002 | Naghavi et al. | | |
| 2003/0182164 A1 | 9/2003 | Shabot et al. | | |
| 2003/0187689 A1 | 10/2003 | Barnes et al. | | |
| 2003/0200226 A1 | 10/2003 | Wells et al. | | |
| 2003/0225597 A1 | 12/2003 | Levine | | |
| 2004/0064343 A1 | 4/2004 | Korpman et al. | | |
| 2004/0073461 A1 | 4/2004 | Pappas | | |
| 2004/0128163 A1 | 7/2004 | Goodman et al. | | |
| 2004/0128165 A1 | 7/2004 | Block et al. | | |
| 2004/0172307 A1 | 9/2004 | Gruber | | |
| 2004/0240720 A1 * | 12/2004 | Brantley et al. | ............. | 382/132 |
| 2005/0002483 A1 | 1/2005 | Wilcox, Jr. | | |
| 2005/0055240 A1 | 3/2005 | Walsh et al. | | |
| 2005/0060192 A1 | 3/2005 | Brown et al. | | |
| 2005/0065824 A1 | 3/2005 | Kohan | | |
| 2005/0108059 A1 | 5/2005 | Tay | | |

* cited by examiner

*Primary Examiner*—Gerald J. O'Connor
*Assistant Examiner*—Neha Patel
(74) *Attorney, Agent, or Firm*—Carrie A. Boone, P.C.

(57) ABSTRACT

A web-based system is disclosed for managing radiology services for one or more medical facilities. The system, comprising both hardware and software components, provides mechanisms by which radiographic images and demographic information about a patient are transmitted to a central location and efficiently combined, allowing a designated radiologist to efficiently interpret the radiographic images and produce a preliminary report. The central location includes web-based, secure access by which multiple entities may interpret and update the preliminary report. Although the system is designed with after-hours radiology services in mind, the system may be employed in radiology departments during regular weekday operation.

24 Claims, 20 Drawing Sheets

Figure 14

| | | | | |
|---|---|---|---|---|
| ⧗ | James Brown<br>CT CHEST + PE | 170 | 102<br>12231 | 168 |
| ⧗ | Mary Douglas<br>CT CHEST + PE<br>SOB | 166 | 103<br>39304 | |
| ☾ | Fred Higgins<br>CT HEAD<br>HTN/HA/WEAKNESS X1DAY | Preliminary Report | 101<br>90372 | 8/23/05 11:15 PM<br>8/23/05 11:39 PM<br>0:24 Dr. Brown |
| ☾ | Karen Johnson<br>CT HEAD<br>WORST HA OF LIFE/NAUSEA | Preliminary Report | 102<br>49391 | 8/23/05 11:28 PM<br>8/23/05 11:54 PM<br>0:25 Dr. Green |
| | Rosemary Peterson<br>90YO/NO HX | | 101<br>94311 | |
| ⧗ | Sam Turner  162  164<br>CT OTHER +OR-<br>L HIP PAIN, BILAT ORIF | | 102<br>78904 | |

— 160

172

AFTER-HOURS RADIOLOGY SYSTEM

FIELD OF THE INVENTION

This invention relates to providing radiology services and, more particularly, to a system and method for managing radiology information online.

BACKGROUND OF THE INVENTION

Radiology is a branch of medicine in which various imaging techniques may be employed to diagnose and treat a wide variety of diseases. Named for the radioactive substances used to produce the images, radiologists, also known as clinical radiologists, may employ many techniques for imaging the patient, including magnetic resonance imaging (MRI), computed tomography (CT, or "cat scan"), ultrasonography (US), nuclear medicine (NM), x-ray/plain film, angiography, and fluoroscopy, to name a few. In addition to their medical education, radiologists receive training in reading and interpreting radiographic images.

To facilitate diagnosis and treatment, a patient's physician, such as a general practitioner, may order one or more radiology tests on the patient. A radiology technologist positions the patient before the imaging apparatus and initiates the imaging function, which produces the radiographic image. Rarely, the patient's physician is capable of interpreting the radiographic image. In many environments, such as hospitals and group practices, the task of interpreting the image is left to the radiologist.

With such division of labor prevalent in medicine, the patient is rarely in communication with the radiologist directly. Thus, before interpreting the radiologist images, the radiologist may prefer or require additional patient information from the physician, such as historical information, known symptoms, and other communication obtained by the patient's physician. Once the radiographic image and the additional patient information are received, the radiologist produces a preliminary report. The patient physician is able to diagnose and treat the patient, in large part, based upon the preliminary report.

Radiographic images are ordered in the diagnosis of a number of different patient maladies. While the patient with a common cold may avoid being imaged, patients with broken bones, pregnant women, and cancer patients routinely obtain radiographic images prior to diagnosis or during treatment. The successful operation of a medical facility, such as a hospital or group practice, therefore, depends on the availability of one or more radiologists at all times and the efficient interpretation of radiographic images by the radiologist.

The availability of radiologists and radiology services during weekends and after-hours (e.g. 5:00 p.m.-7:00 a.m.) may be particularly problematic, as many facilities do not have a radiologist present during these hours. Further, many physicians may not have radiology equipment (even x-ray machines) on-site, and may thus send the patient to a radiology laboratory to obtain the images, which are then returned to the diagnosing physician. The delays associated with these conditions may impair the ability of the diagnosing physician to successfully and timely treat the patient.

In the past, radiology clinics principally employed printed film to capture the radiographic image, which the radiologist then physically hung on "view boxes" to illuminate the image. Today, many of the radiographic images generated using the techniques enumerated above may be stored digitally and viewed on computer displays.

A model known as Patient Archiving and Communication System, or PACS, is employed in some medical facilities. Under PACS, radiographic images are stored on computer media, viewed on displays, and manipulated using radiology-specific software. This eliminates the need to print the radiographic image on film (which is expensive); instead, the radiographic images are stored electronically at significant cost savings. PACS has significantly reduced the time and energy required to prepare the images for evaluation, allows the images to be viewed from multiple computer-system-based sources, allows the images to be viewed simultaneously by many users at different locations, and allows side-by-side comparison of images. The radiographic images may be transferred electronically, rather than being delivered by couriers to their destinations. Some PACS implementations additionally integrate dictated reports with the radiographic images and the patient's hospital information. Combining images and reports can be an expensive and complicated process under PACS, however. Unfortunately, there are a number of vendors that provide proprietary PACS solutions, many of which are incompatible with one another.

Thus, there is a continuing need to improve radiological services so as to facilitate patient diagnosis and treatment.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein like reference numerals refer to like parts throughout the various views, unless otherwise specified.

FIG. 14 is a patient list presented along with the display interface of FIG. 13, according to some embodiments;

DETAILED DESCRIPTION

In accordance with the embodiments described herein, a web-based system is disclosed that manages radiology services for one or more medical facilities. The system, comprising both hardware and software components, provides mechanisms by which radiographic images and demographic information about a patient are transmitted to a central location and efficiently combined, allowing a designated radiologist to efficiently interpret the radiographic images and produce a preliminary report. The central location includes web-based, secure access by which multiple entities may interpret and update the preliminary report. Although the system is designed with after-hours radiology services in mind, the system may be employed in radiology departments during regular weekday operation.

In the following detailed description, reference is made to the accompanying drawings, which show by way of illustration specific embodiments in which the invention may be practiced. However, it is to be understood that other embodiments will become apparent to those of ordinary skill in the art upon reading this disclosure. The following detailed description is, therefore, not to be construed in a limiting sense, as the scope of the present invention is defined by the claims.

Figure 1:
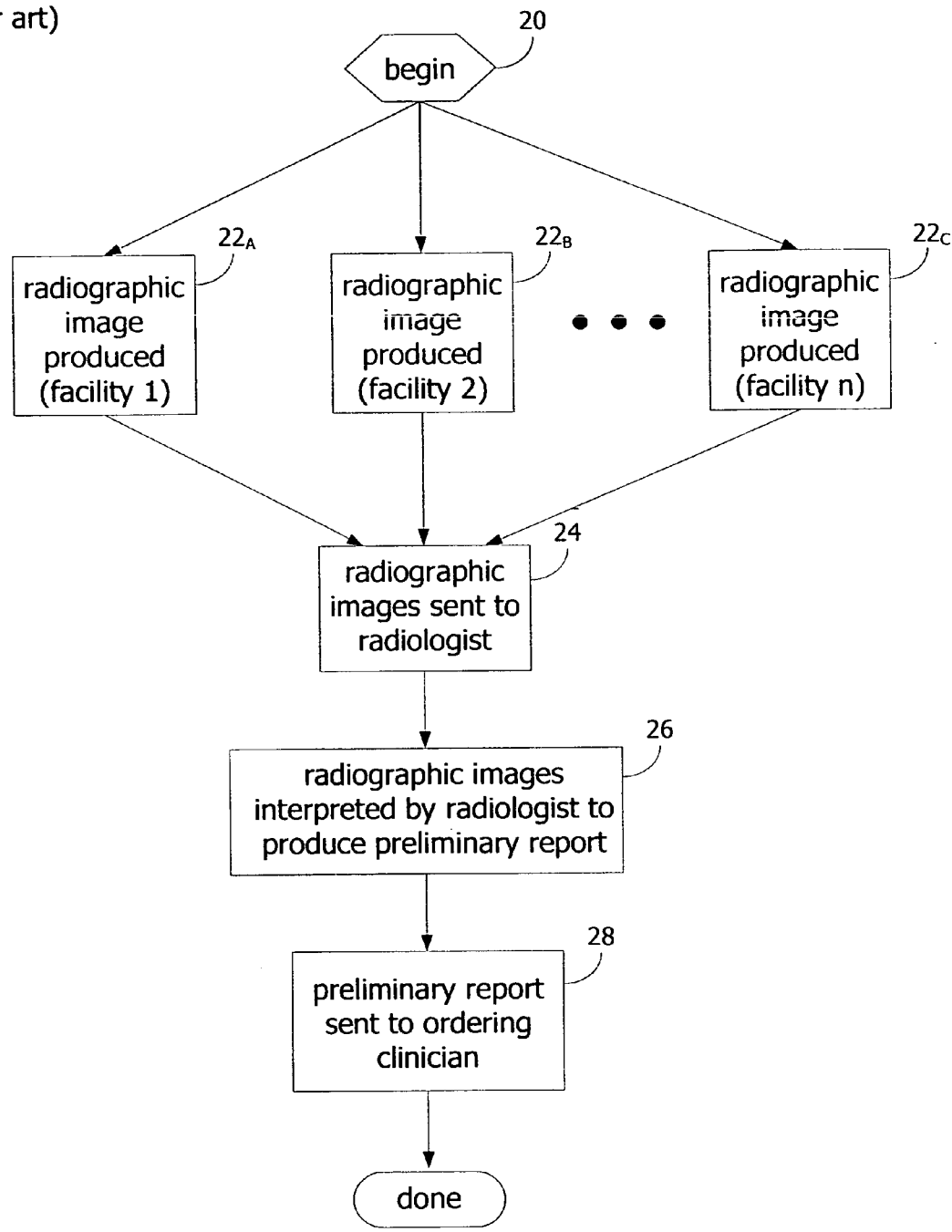
FIG. 1 is a flow diagram of a workflow process for providing radiology services, according to the prior art.

In FIG. 1, a flow diagram depicts a workflow process 20 of a typical radiology clinic, according to the prior art. The workflow process 20 begins when radiographic images are produces. Multiple radiographic images may be received by the radiology clinic from multiple facilities. In FIG. 1, for example, there are n facilities, for integer n. A radiographic image is produced from a first facility (block 22A), a radiographic image is produced from a second facility (block 22B), and a radiographic image is produced from an nth facility (block 22C).

The radiographic images are then sent to the radiologist (block 24). Transmission may be by courier or regular mail, with an associated time delay. Where the facility is PACS-compatible, the radiographic images may be digital in form, and thus transmissible via email or through a web-based interface. (Transmission by facsimile is not an option for radiographic images.) Receipt of the radiographic images from each facility (blocks 22A, 22B, and 22C) may be sequential or simultaneous. The processing of the images is likely to be sequential, possibly on a first-come-first-served basis, by the radiologist, unless multiple radiologists are available at the radiology clinic.

Upon receipt of each radiographic image, the radiologist interprets the image and produces a preliminary report (block 26). The preliminary report is then sent to the ordering clinician, whether the patient's physician or some other individual (block 28). As with the radiographic images, the transmission of the preliminary report may be by courier, regular mail, electronic mail, or via a web-based access. The preliminary report may also be sent to the patient's physician via facsimile transmission.

The workflow process 20 of FIG. 1 is traditionally how after-hours radiology services are provided, since radiologists are often physically present at a medical facility during normal business hours, but not after hours. However, the prior art workflow process 20 generally depicts the flow of information that takes place in order for the radiologist to generate the work product, whatever the time of day: receipt of radiographic images by the radiologist, interpretation of the images, and production of the preliminary report by the radiologist.

The prior art workflow process 20 is disadvantageous for several reasons. For one, the radiologist lacks additional information about the patient that may facilitate or enhance the interpretation of the radiographic image. Keeping track of which facility sent each radiographic image may complicate the transmission of preliminary reports to the appropriate ordering clinician. The time delay associated with the transmission of the radiographic image and the subsequent preliminary report is often undesirable. Under the workflow process 20, the radiologist is unable to communicate with the patient's physician, who may or may not be the ordering clinician. The preliminary report itself lacks a mechanism for including feedback/comments from other doctors.

Radiology System

Figure 2:
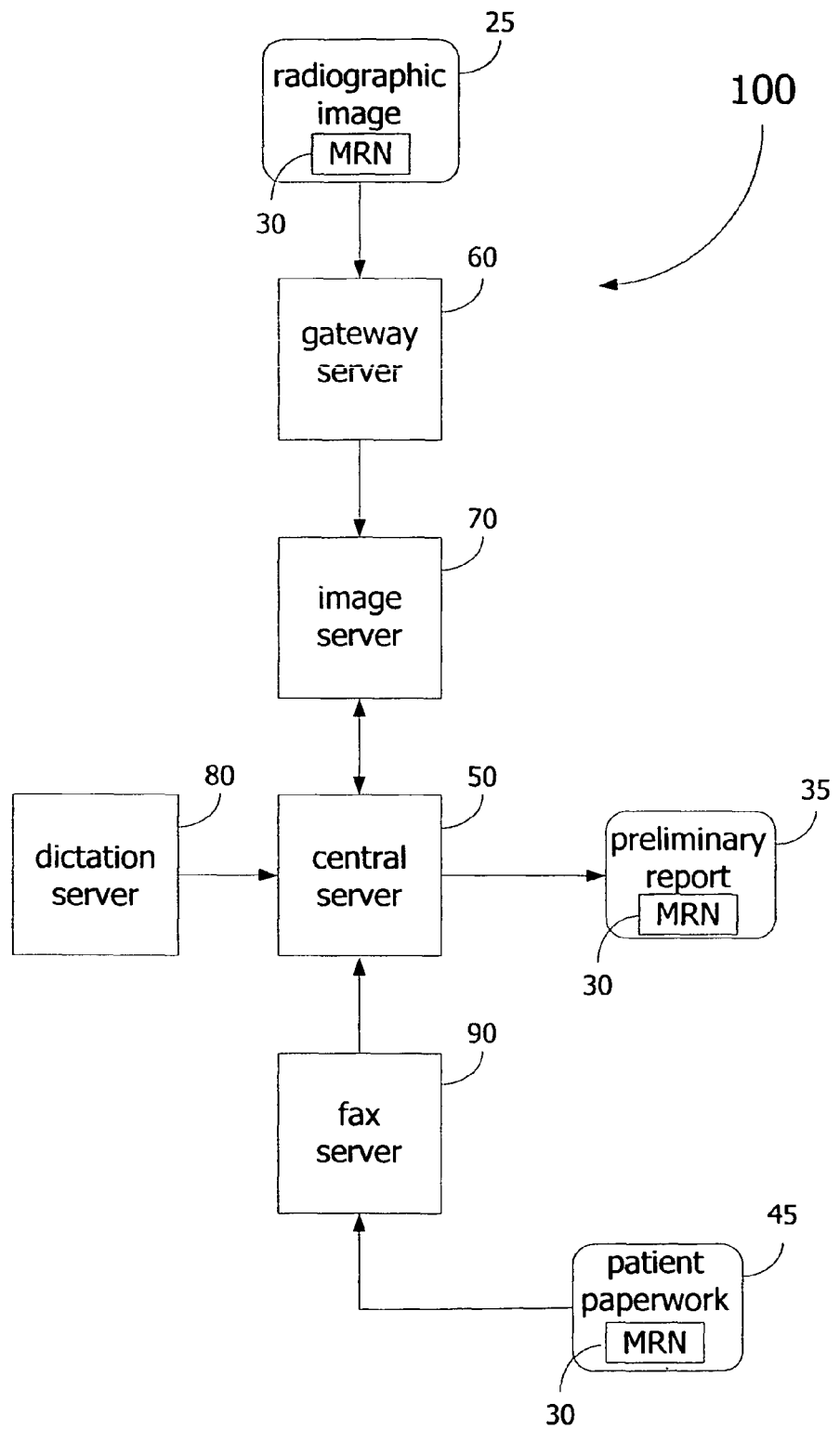
FIG. 2 is a block diagram of a system for providing radiology services, according to some embodiments.

In FIG. 2, according to some embodiments, an alternative to the prior art workflow process 20 is disclosed, according to some embodiments. A radiology system 100, comprising both software and hardware components, is capable of providing radiology support, particularly after hours, for one or more medical facilities. The radiology system 100 includes five servers: a gateway server 60, an image server 70, an optional dictation server 80, a central server 50, and a fax server 90. The radiology system 100 receives a radiographic image 25 and patient paperwork 45 as inputs, and produces a preliminary report 35 as its output. Information stored on and generated by the radiology system 100 is accessible via a secure, web-based interface, providing access thereto by one or more radiologists, clinicians, and other medical professionals. The servers of the radiology system 100 are arranged so that both the radiographic image 25 and the patient paperwork 45 may be quickly accessible to the central server 50, allowing the radiologist to simultaneously access both documents 25 and 45, and thus produce the preliminary report 35.

Gateway Server

Figure 3:
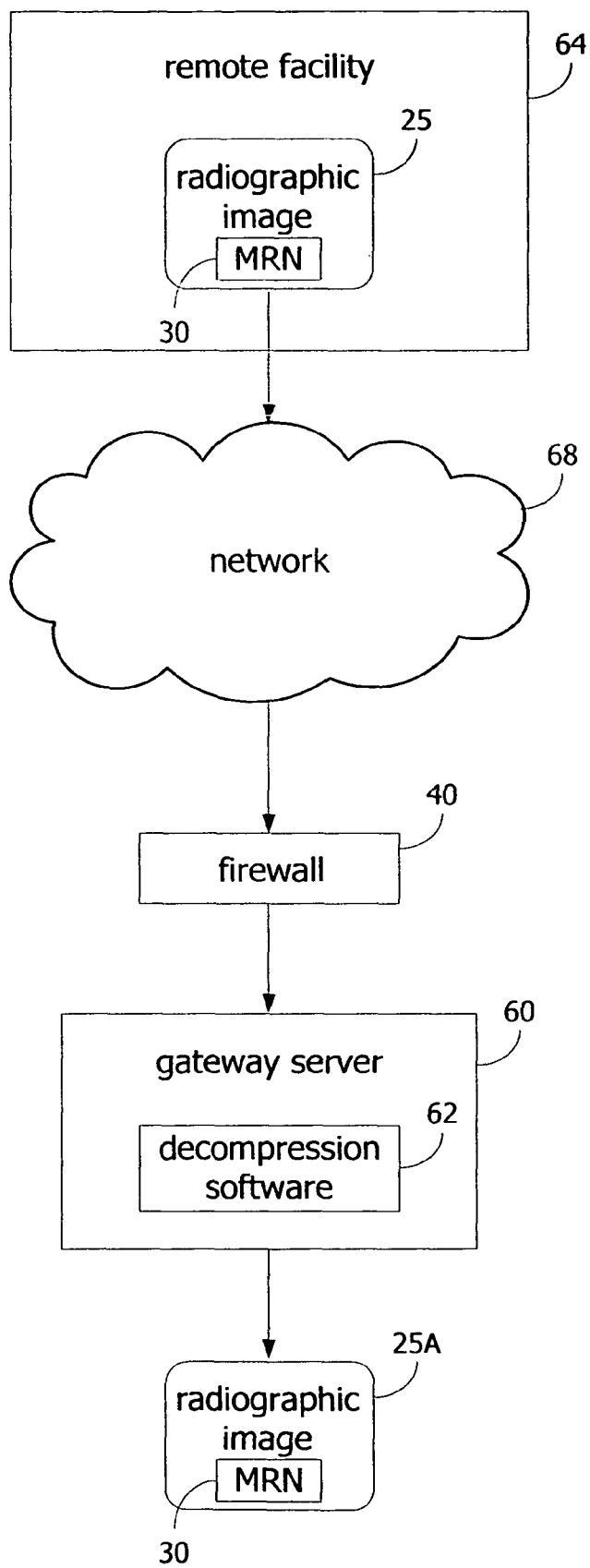
FIG. 3 is a block diagram of the gateway server of the radiology system of FIG. 2, according to some embodiments.

Referring additionally to FIG. 3, the gateway server 60 of FIG. 2 receives the radiographic image 25 from a remote facility 64 across a network 68. As used herein, remote facility is described in reference to the radiology system 100, and may refer to any facility that is coupled to the radiology system via a network. Where the servers of the radiology system 100 (FIG. 2) occupy a first room and radiology services, such as x-ray imaging, occupy a second room which is adjacent to the first room, where the x-rays are transmitted to the first room across a network, the second room is deemed a remote facility for purposes of this discussion. The network 68 may be a private network, such as an Intranet of a medical facility, or a wide-area network, such as the Internet.

The servers within the radiology system 100 constitute a private network. Therefore, prior to being received into the servers, the radiographic image 25 passes through an optional firewall 40, to prevent unauthorized access to the radiology system 100. The gateway server 60 thus operates as a gateway into the network of radiology system servers. Although depicted as a distinct component in the radiology system 100, the firewall 40 may be part of the gateway server 60. The firewall 40 may include hardware, software, or a combination thereof to prevent unauthorized access to the radiology system 100 from across the wide-area network 68.

In some embodiments, the radiographic image 25 is compressed at the one or more medical facilities prior to being transmitted to the radiology system 100. The gateway server 60 thus receives the radiographic image 25 in compressed form. Compressing before transmission over the wide-area network facilitates speedy transmission of the radiographic image 25 to the radiology system 100. Upon receipt, the gateway server 60 includes decompression software 62, which decompresses the radiographic image 25 (if compressed), producing decompressed radiographic image 25A, which will be transmitted to the image server 70. (For simplification, unless otherwise specified, references to radiographic images 25, once part of the radiology system 100, are understood to refer to the decompressed radiographic images 25A shown in FIG. 3.)

Image Server

Figure 4:
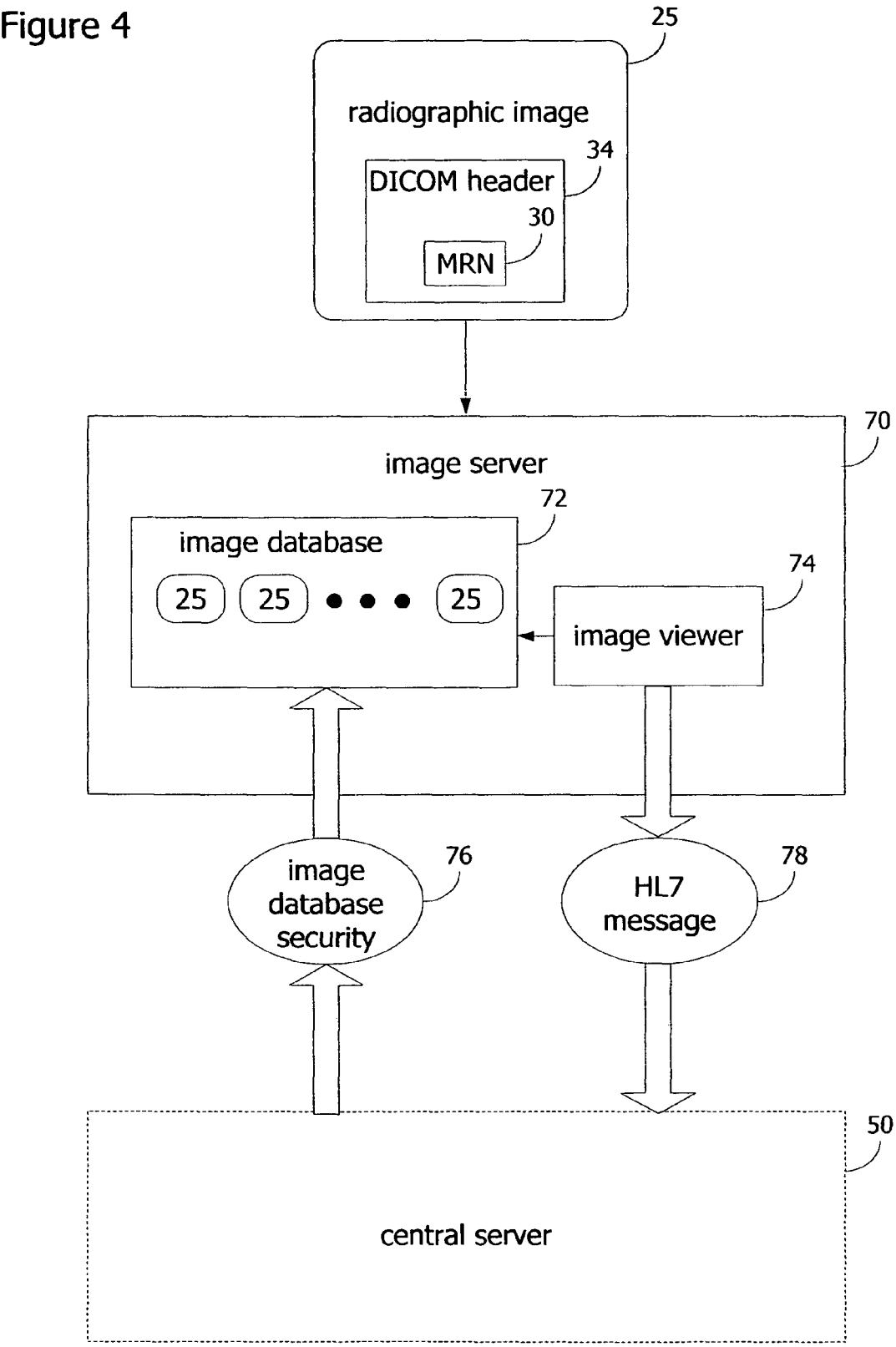
FIG. 4 is a block diagram of the image server of the radiology system of FIG. 2, according to some embodiments.

Returning to FIG. 2, the radiology system 100 also includes an image server 70. Referring also to FIG. 4, the image server 70 receives the decompressed radiographic image 25 from the gateway server 60 in the radiology system 100 of FIG. 2. The image server 70 includes an image database 72, upon which each decompressed radiographic image 25 is stored. Since the radiographic images may be quite large in size (e.g., 50 megabytes each), the image database 72 may also be very large. In some embodiments, the image database 72 is at least one terabyte in size. As will be shown, the image database 72 is accessible by the central server 50 for retrieving one or more radiographic images 25 stored thereon. In some embodiments, the image database 72 is secured, so as to be accessible by entering a password, a username/password combination, or via some other security measure (shown in FIG. 4 as image database security 76). As will be shown, access to the central server 50 includes security features for limiting access to the radiology system 100. In some embodiments, the security measures used to limit access to the central server 50 obviate the need for image database security 76.

In some embodiments, the radiographic images 25 stored on the image database 72 are maintained for up to a predetermined time period, such as six months, or until the server 70 is full, whichever condition occurs first. Radiographic images 25 may be stored in a first-in-first-out arrangement, or may be maintained according to a designated priority. Alternatively, the radiographic images 25 may be routinely copied to removable media and stored off-site indefinitely, as desired.

Also depicted in FIG. 4, the image server 70 includes an image viewer 74. The image viewer 74 reads a header, shown as a DICOM header 34 in FIG. 4, from the radiographic image 25, extracts an MRN 30 of the patient, and sends an HL7 message to the central server 50. HL7, or "health level seven," is a protocol for exchanging information between medical applications. HL7 defines the format and the content of the messages that medical applications use when exchanging data with one another in various circumstances. One benefit to using HL7 in a medical facility is that patient information may be entered in a single application, then easily ported and shared between applications without having to re-enter the information. The radiology system 100 uses HL7 in communicating between the image server 70 and the central server 50.

As depicted in FIG. 2, the radiographic image 25, patient paperwork 45, and preliminary report 35 each include an MRN 30. The MRN 30 is a medical record number of the patient for whom radiology services are being provided. Medical record numbers are universally used in medical facilities to maintain accurate record-keeping of patient information, as well as to ensure patient privacy. The MRN 30 from both the radiographic image 25 and from the patient paperwork 45 will be used to match the documents together, thus facilitating efficient production of the preliminary report 35 by the radiologist.

In some embodiments, the incoming radiographic image 25 includes a header that conforms to the Digital Imaging and Communications in Medicine (DICOM) standard. This standard was created by the National Electrical Manufacturers Association (NEMA) to facilitate the distribution and viewing of radiographic images. As shown in FIG. 4, the radiographic image 25 includes the DICOM header 34. The DICOM header 34 includes information about the patient, such as the patient's name, as well as information about the radiographic image 25, such as scan type, image dimensions, and so on. The DICOM header also includes the patient MRN 30. For each patient, once patient information is obtained, each radiographic image 25 will include the complete patient information in the DICOM header 34.

Each time a radiographic image 25 is received by the image server 70, the image viewer 74 extracts patient demographic information from the DICOM header 34 and produces an HL7 message 78 containing the information. Patient demographic information may include the patient's name, age, sex, medical record number (MRN), date of study, hospital of origin, history, and referring physician. The HL7 message 78 is then sent to the central server 50. As will be shown, the HL7 message 78 is subsequently used by the radiology system 100 to match the radiographic image 25 to patient paperwork 45 received from the fax server 90. In some embodiments, the image viewer 74 consists of eMed.net Enterprise software. (eMed.net Enterprise software is a product of eMed Technologies of Burlington, Mass.)

Figure 5:
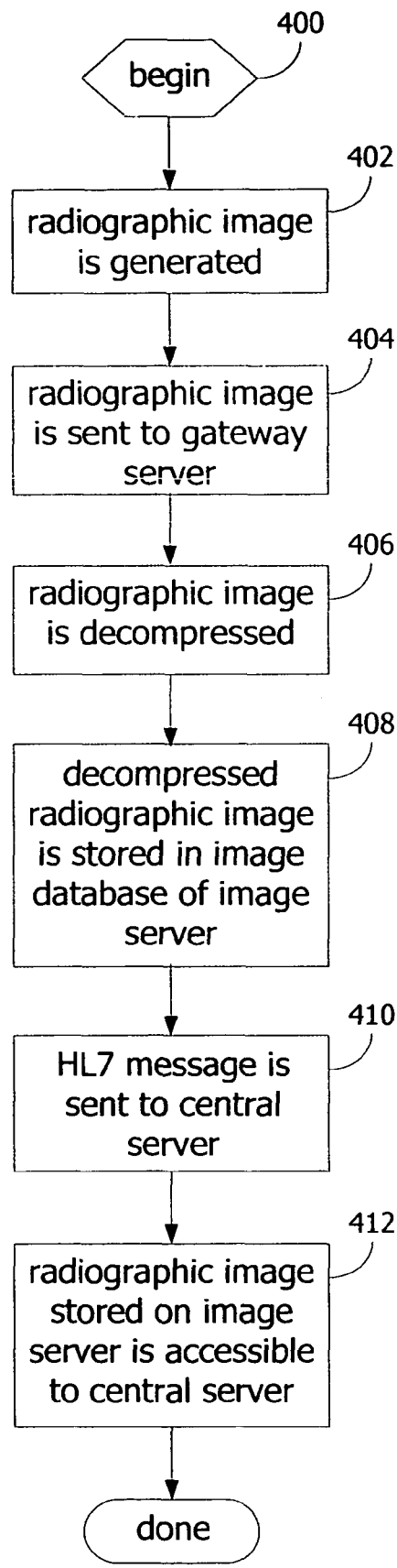
FIG. 5 is a flow diagram of a process for retrieval of the radiographic image used by the radiology system of FIG. 2, according to some embodiments.

With reference also to FIGS. 3 and 4, FIG. 5 is a flow diagram describing the aforementioned process for obtaining and storing the radiographic image 25 obtained by the radiology system 100 from a remote facility, as defined above, according to some embodiments. Although the operations are depicted as occurring in a particular order, one or more operations may occur in a different sequence, as those of ordinary skill in the art will recognize, without departing from the spirit of the disclosure.

The radiographic image is generated at a remote facility (block 402). The remote facility may be a hospital, a group practice, or other site in which radiographic images of patients are obtained; the radiographic image 25 may be an MRI, a cat scan, ultrasound, nuclear medicine, or x-ray, or other type of radiographic image. Optionally, the radiographic image 25 passes through a firewall 40, and is then transmitted to the gateway server 60 (block 404). In some embodiments, the radiographic image 25 is compressed at the remote facility, prior to transmission to the gateway server 60. At the gateway server 60, the radiographic image 25 is decompressed (block 406), using the decompression software 62 loaded on the gateway server 60. The decompressed radiographic image is transmitted to the image server 70 and stored on its image database 72 (block 408).

Once the radiographic image 25 is stored on the image server 70, the image viewer 74 generates an HL7 message 78 containing pertinent patient information obtained from the DICOM header 34 of the radiographic image 25, then send the HL7 message 78 to the central server 50 (block 410). The radiographic image 25, still stored on the image server 70, is thus available to the central server 50 for viewing (block 412).

Dictation Server

Figure 6:
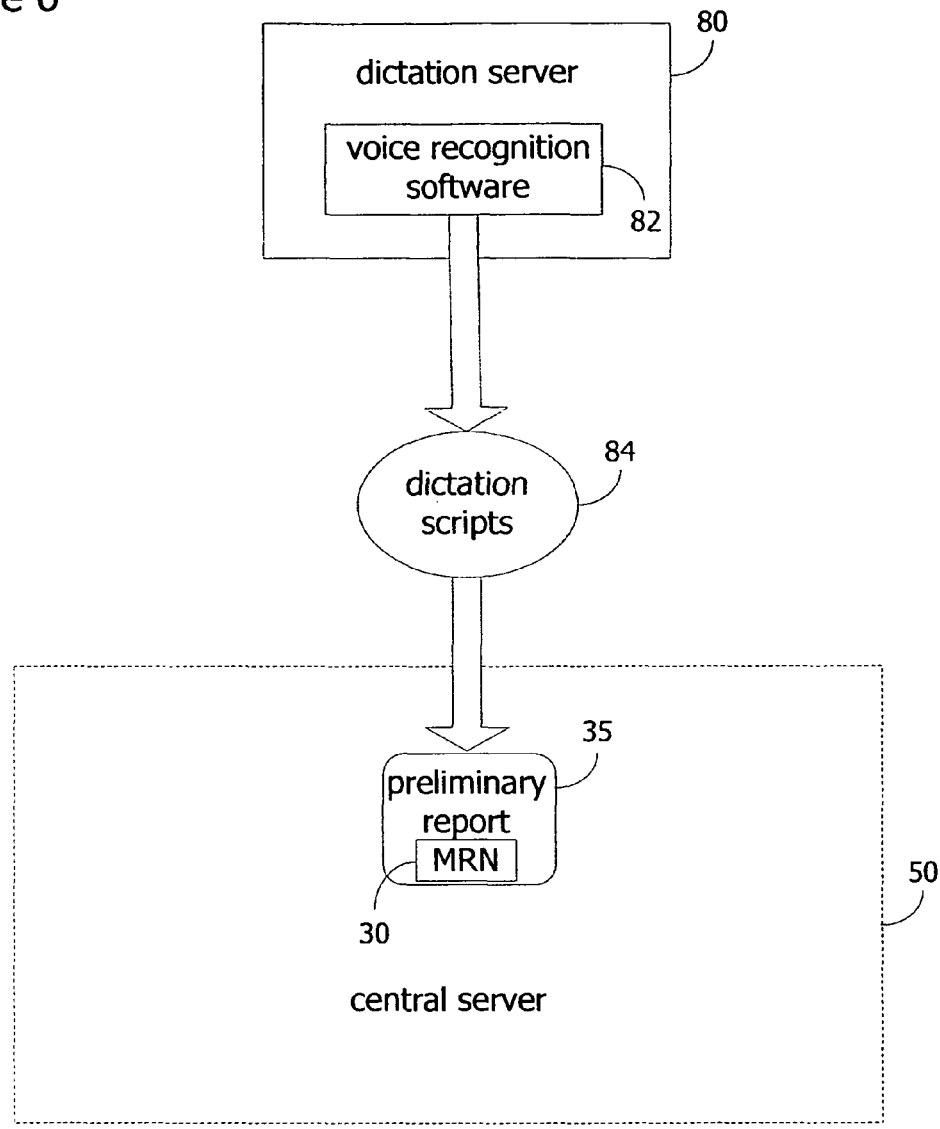
FIG. 6 is a block diagram of the dictation server used in the radiology system of FIG. 2, according to some embodiments.

Returning to FIG. 2 and also referring to FIG. 6, the dictation server 80 is an optional feature of the radiology system 100 of FIG. 2. The dictation server 80 includes voice recognition software 82, to facilitate the completion of the preliminary report 35 by the radiologist. The voice recognition software 82 generates dictation scripts 84, which populate predefined fields of the preliminary report 35. (The preliminary report 35 is further described in the depiction of FIG. 15, below.) In some embodiments, the voice recognition software 82 is PowerScribe v4.7 SDK kit v.1.4. (PowerScribe is a product of Dictaphone Corporation of Stratford, Conn.)

Fax Server

Figure 7A:
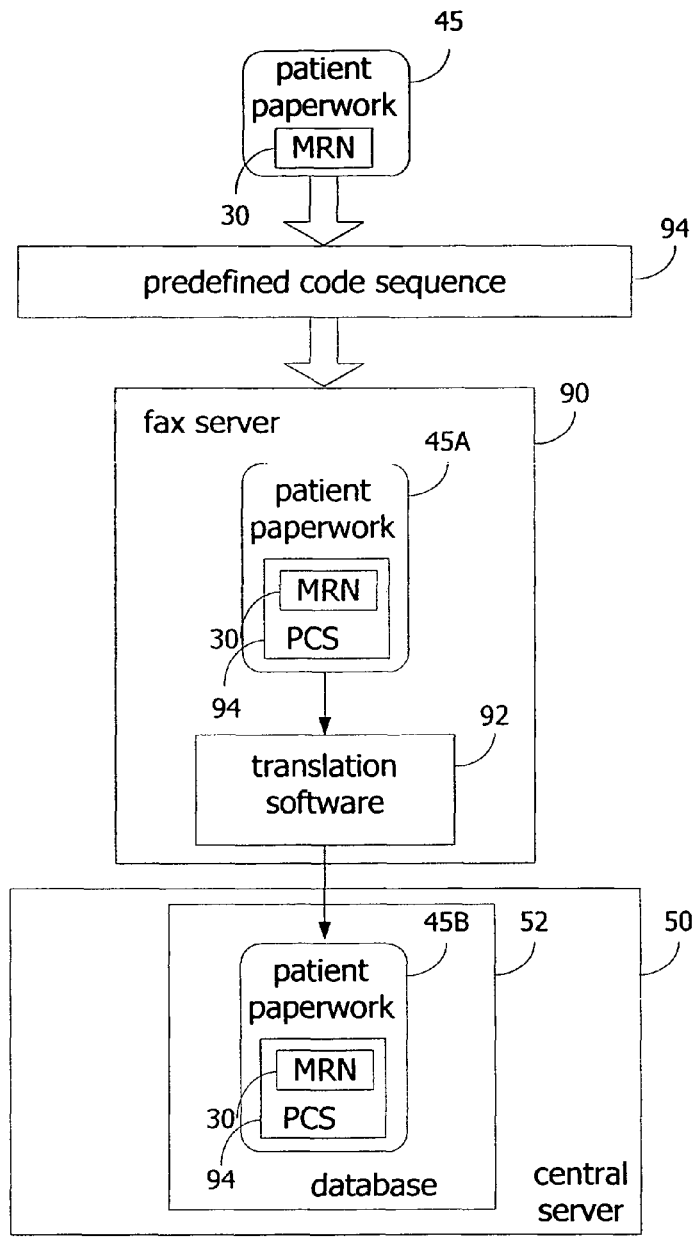
FIG. 7A is a block diagram of the fax server used in the radiology system of FIG. 2, according to some embodiments.
Figure 7B:
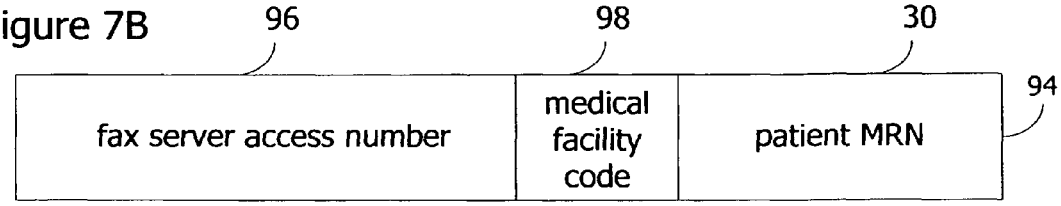
FIG. 7B is a block diagram of the predefined code sequence used to access the fax server of FIG. 7A, according to some embodiments.

As shown in FIG. 2, and referring also to FIGS. 7A and 7B, the radiology system 100 receives the patient paperwork 45 produced at the medical facility using the fax server 90. The fax server 90 accepts the patient paperwork 45 from the one or more medical facilities serviced by the radiology system 100.

The patient paperwork 45 may include virtually any information about the patient that is provided by the medical facility, such as the radiology request itself, which includes information about the patient and indicates which studies are to be conducted on the patient. During the patient scan of the radiology image 25, the radiology technician may record additional information on the radiology request, such as patient comments about pain, historical information, and so on. Such information is preferably made available to the radiologist, and thus is considered part of the patient paperwork 45. The patient paperwork 45 may be presented in a variety of formats, whether it be a proprietary format created by the medical facility, a proprietary format generated by the radiology system 100, or notes written on a piece of paper. In FIGS. 2 and 7A, the patient paperwork 45 is depicted as including the MRN 30 of the patient. In some embodiments, the patient paperwork 45 (which may or may not include the MRN in the document) is faxed using a predefined code sequence 94, part of which includes the patient's MRN.

One predefined code sequence 94 is depicted in FIG. 7B, according to some embodiments. The individual at the medical facility who sends the patient paperwork 45 to the fax server 90 does so by entering the predefined code sequence 94 into a fax machine located at the medical facility, then sending the patient paperwork 45 as a fax transmission. The predefined code sequence 94 includes three components: a fax server access number 96, a medical facility code 98, and the unique patient MRN 30 associated with the patient for whom radiology services are being requested.

The fax server access number 96 may be a local telephone fax number (seven- or ten-digit) or a toll-free telephone number, such as an "800" number. The medical facility code 98 is a unique numerical sequence that is assigned to the requesting medical facility, such as a hospital. In some embodiments, the medical facility code 98 is a three-digit number. The patient MRN 30 is actually an abbreviated portion of the actual patient MRN, which may be many digits in length. In some embodiments, the patient MRN 30 consists of the last five digits of the actual patient MRN.

By including the patient MRN 30 in the sequence of numbers dialed by the requesting individual, the need to scan the patient paperwork 45 to obtain the patient MRN may be avoided. In some environments, the fax machine at the medical facility can be programmed to "speed dial" the fax server access number 96 and the medical facility code 98, such that the requesting individual may append the patient MRN 30 to the end of the speed dial sequence prior to sending the patient paperwork 45 to the fax server 90. In some embodiments, the fax server 90 has a "roll-over" provision of one or more additional fax server access numbers 96, to avoid a failure where simultaneous fax transmissions are made to the radiology system 100. Once the patient paperwork 45 is received by the fax server 90, the predefined code sequence (PCS) 94 used to access the fax server is associated with the patient paperwork. Thus, in FIG. 7A, patient paperwork 45A is depicted with the PCS 94 used to transmit the patient paperwork 45 to the fax server 90, wherein the patient MRN 30 is embedded in the PCS 94.

In addition to coupling incoming patient paperwork 45 with an associated PCS 94, the fax server 90 optionally includes translation software 92, which converts the faxed patient paperwork 45A into a preferred format. (The translated paperwork is shown in FIG. 7A as patient paperwork 45B). In some embodiments, the translation software 92 converts the faxed patient paperwork 45A into TIFF files (tagged image file format). In other embodiments, the translation software 92 converts the faxed patient paperwork 45A into PDF files (portable document format). The fax server 90 then transmits the converted patient paperwork 45B to the central server 50. (For simplification, unless otherwise specified, references to patient paperwork 45, once part of the radiology system 100, are understood to refer to the appended and translated patient paperwork 45B shown in FIG. 7A.) The patient paperwork 45 is stored, along with the unique PCS 94, on a database 52 located on the central server 50. In some embodiments, the PCS 94 operates as a pointer to its associated patient paperwork 45, providing efficient access to the paperwork during subsequent operations.

Figure 8:
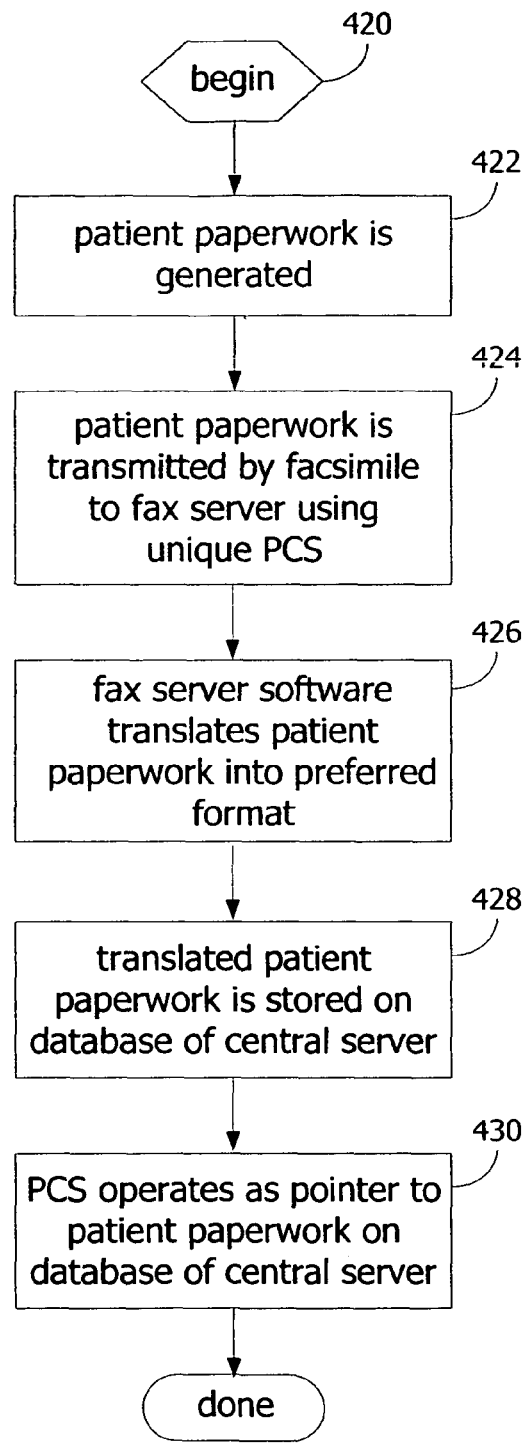
FIG. 8 is a flow diagram of a process for retrieval of the patient paperwork used by the radiology system of FIG. 2, according to some embodiments.

With reference also to FIGS. 7A and 7B, FIG. 8 is a flow diagram describing the aforementioned process for obtaining and storing the patient paperwork 45 obtained by the radiology system 100 from a remote facility, as defined above, according to some embodiments. The operations of FIG. 8 may occur simultaneously with those in the flow diagram of FIG. 5, above, may precede the operations of FIG. 5, or may follow the operations of FIG. 5. Furthermore, although the operations are depicted as occurring in a particular order, one or more operations may occur in a different sequence, as those of ordinary skill in the art will recognize, without departing from the spirit of the disclosure.

The patient paperwork 45 is generated at a remote facility (block 422). As described above, the patient paperwork 45 includes the request for radiology services, and may be a prescribed form or a hand-written document. The patient paperwork 45 is conveyed to fax server 90 of the radiology system 100 by facsimile transmission, with the sender at the remote facility entering a unique predefined code sequence (PCS) 94 (block 424). Recall that the PCS 94 includes the fax server access number 96, the medical facility code 98 (unique number assigned to the remote facility), and some portion of the patient's medical record number (MRN) 30. The patient paperwork 45 and the PCS 94, once part of the radiology system 100, remain in association with one another.

In some embodiments, the fax server 90 translates the incoming patient paperwork 45 into a preferred format, such as a TIFF or PDF file (block 426). The translated patient paperwork 45 is stored on the database 52 of the central server 50 (block 428). The patient paperwork 45 continues to be associated with the unique PCS 94 used to transmit the paperwork to the radiology system by facsimile. Since the database 52 may store many hundreds or more documents, the PCS 94 provides a facile mechanism for retrieving patient paperwork 45 (block 430).

Central Server

Figure 9:
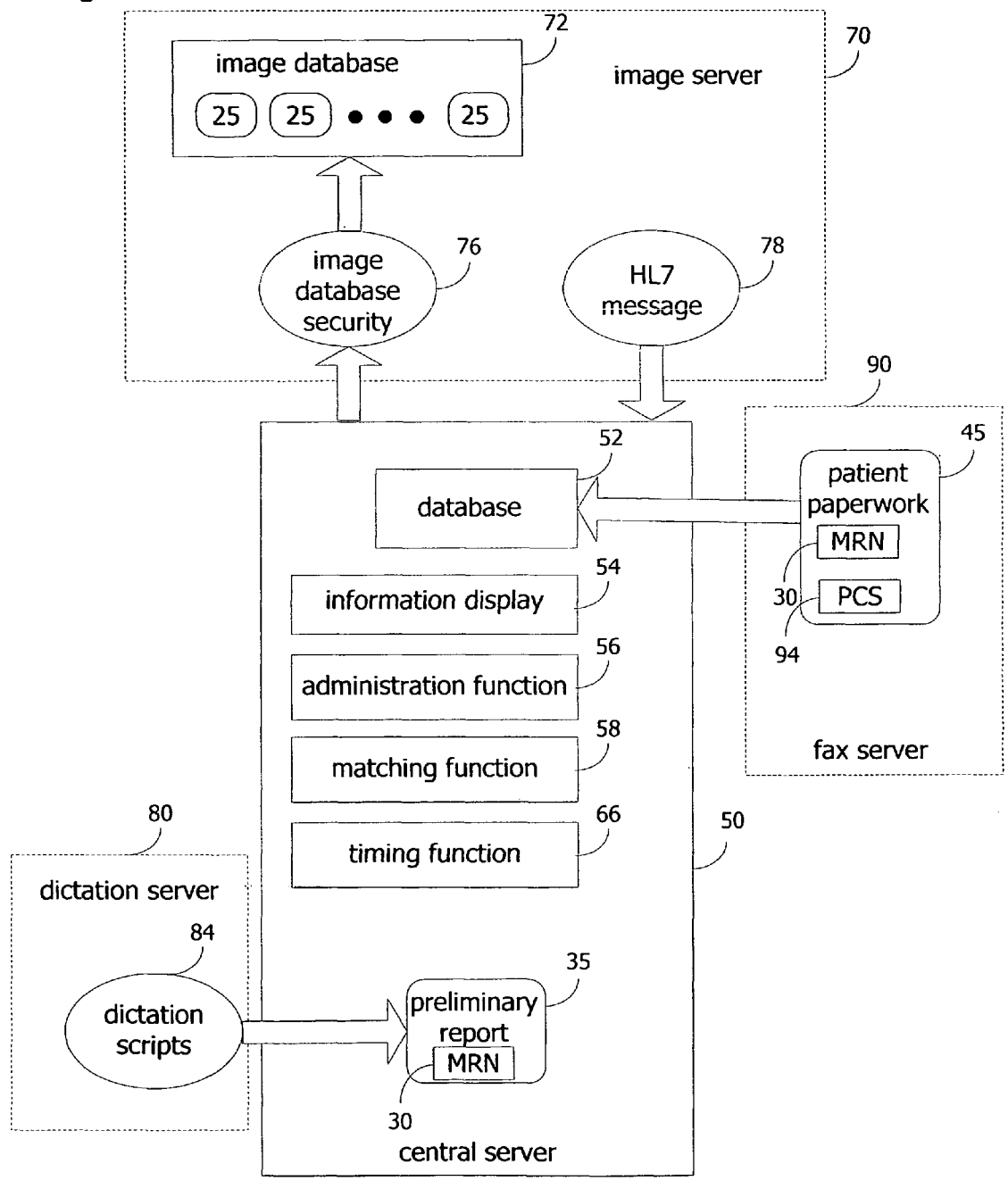
FIG. 9 is a block diagram of the central server of the radiology system of FIG. 2, according to some embodiments.

Returning to FIG. 2 and referring also to FIG. 9, the central server 50 communicates with the image server 70 (to retrieve the radiographic images 25 from the image database 72), the dictation server 80 (to receive dictation scripts 84 produced by the voice recognition software 82), and the fax server 90 (to receive the patient paperwork 45). In FIG. 9, the patient paperwork 45, which may have been converted into a preferred format by the translation software 92 of the fax server 90, is to be stored on a database 52 of the central server 50. The radiographic images 25, still residing on the image database 72 of the image server 70, are accessible to the central server 50 using image database security 76, such as a username and password.

Figure 13:
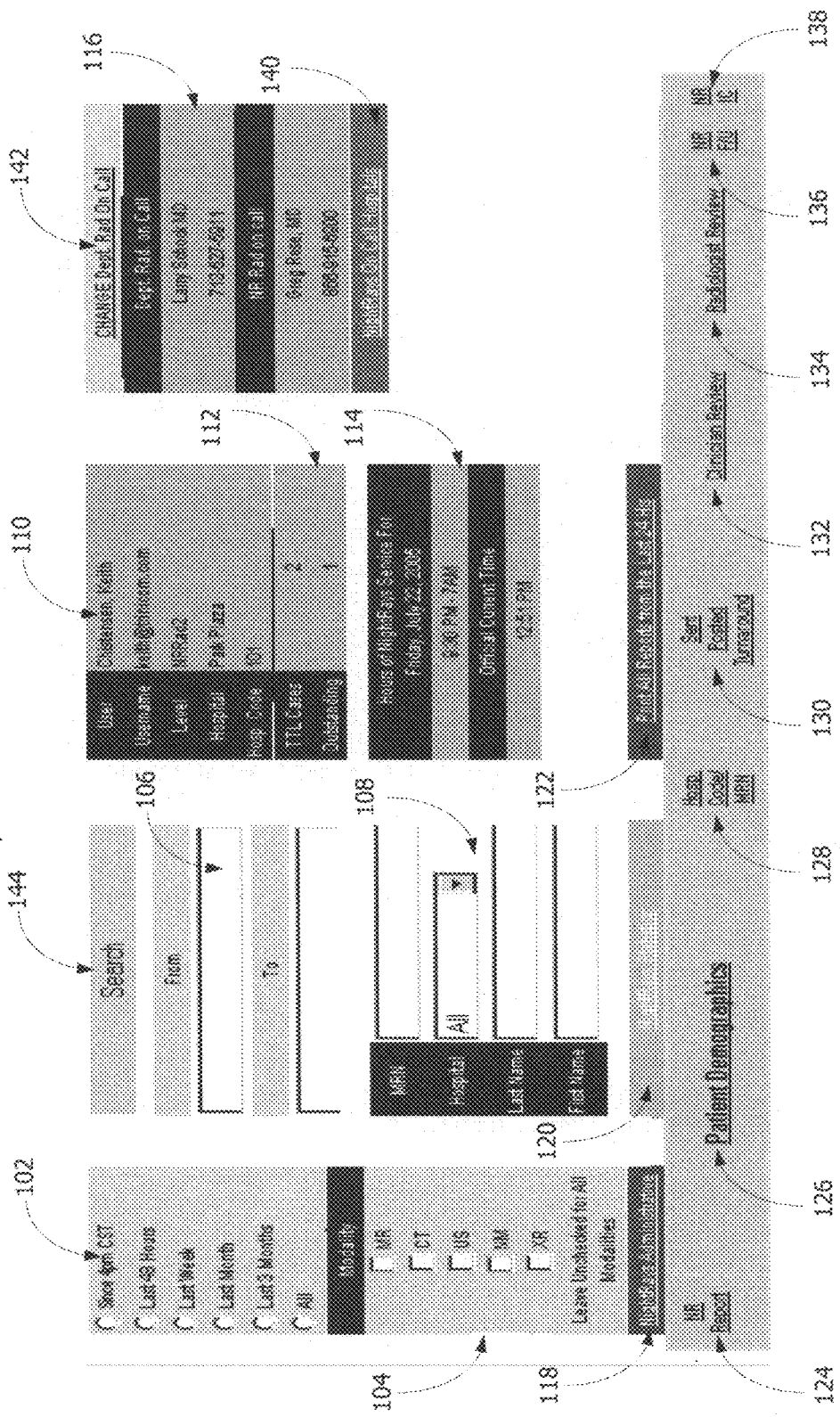
FIG. 13 is a snap-shot of a display interface of the radiology system of FIG. 2, according to some embodiments.

To facilitate production of the preliminary report 35 by the radiologist, the radiographic image 25 of the patient and the patient paperwork 45 are accessible from the central server 50 by way of user interface software 54. The user interface software 54 produces one or more web pages, including a display interface 150, as depicted in FIG. 13, below. As the radiologist is producing the preliminary report 35, dictation scripts 84 generated by the voice recognition software 82 on the dictation server (FIG. 6), may be used to populate predefined fields of the preliminary report, as described further in conjunction with FIG. 15, below.

In addition to the above-described activities, the radiology system 100 further includes an administrative function 56, a matching function 58, and a timing function 66 as part of the central server 50. The administrative function 56 provides administrative services, such as managing and validating user accounts, billing, scheduling, and so on. The administrative function 56 is described further in connection with FIG. 13, below. The matching function 58 matches the radiographic images 25 with the patient paperwork 45, by extracting the MRN 30 from the images and matching it to the paperwork 45, specifically the associated PCS 94, which was faxed using the same MRN 30. The matching function 58 is described in more detail in connection with FIGS. 11 and 12, below. The timing function 66 keeps track of time delays between receipt of information (25 and 45) and production of the preliminary report 35 for each patient in the radiology system 100. The idea of the timing function 66 is to encourage speedy production and review of the preliminary report 35 for all patients. The timing function 66 is described in more detail below.

Patient Status Icons

The above paragraphs discuss how the radiology system 100 obtains both radiographic images 25 and patient paperwork 45 from a remote facility so that the radiologist can generate a preliminary report 35 for the patient. The radiology system 100 is thus designed with the radiologist in mind. However, other individuals may use the radiology system, including, but not limited to, the ordering clinician, the radiologist technician, the patient physician, staff working at the remote facility, and so on.

To serve the many individuals who may use the radiology system 100, the radiology system 100 includes an attractive user interface, which includes a combination of textual and graphical information designed to quickly convey information that is stored and processed in the system. Predefined and color-coded visual indicators, or icons, provide information about the availability of the preliminary report 45, or status, for a given patient. For those who use the radiology system 100 regularly, the icons provide a familiar visual indicator with which the user can readily identify the status of the patient.

Figure 10:
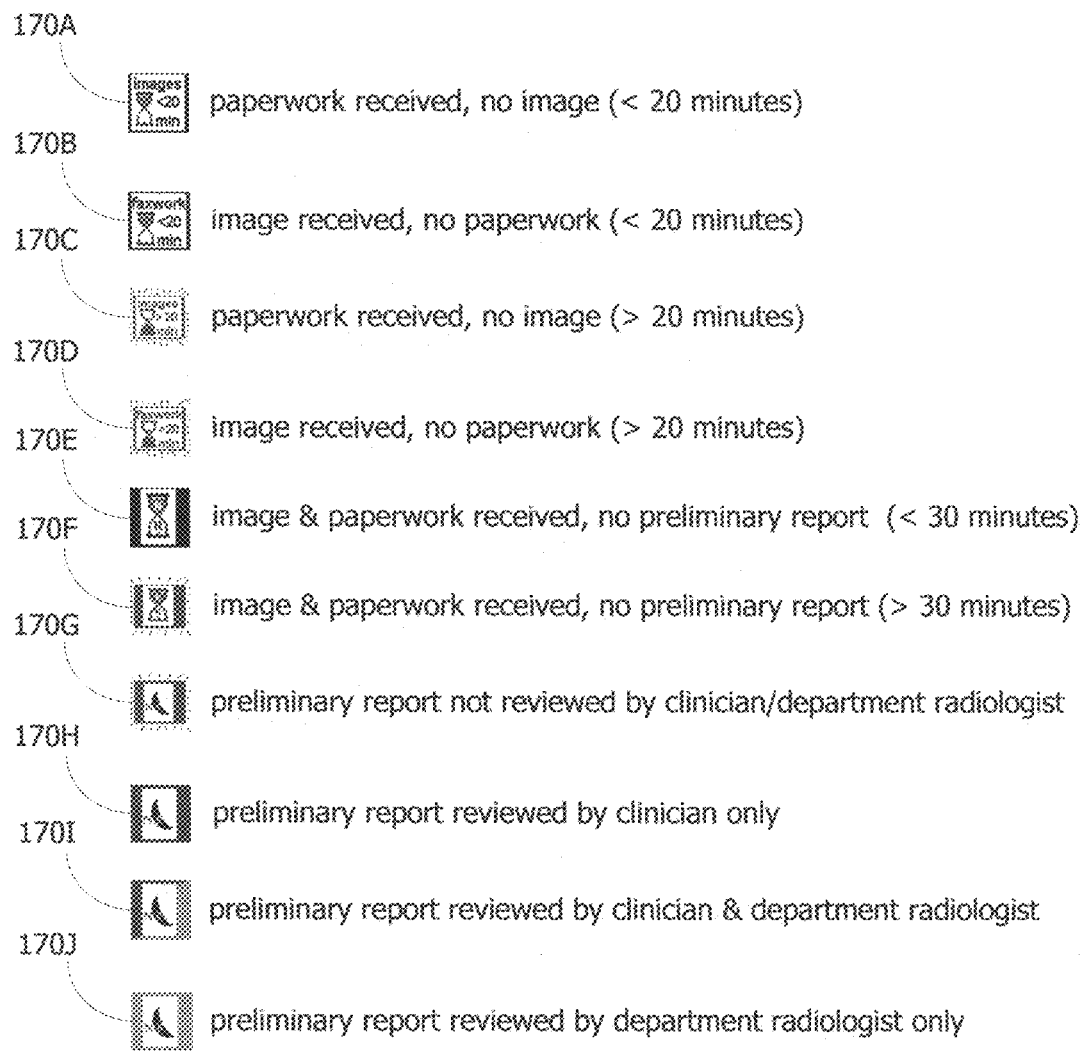
FIG. 10 is a table of icons and their associated meaning for use in the radiology system of FIG. 2, according to some embodiments.

In FIG. 10, according to some embodiments, a list of status icons for use within the radiology system 100 is shown. Icons 170A-170J (collectively, icons 170) are presented, along with the associated meaning for each. Each patient received into the radiology system 100 is associated with one of the icons 170. The icons 170 of FIG. 10 make use of both graphical information and color, to facilitate quick identification of patient status. Icons 170A, 170B, 170C, and 170D indicate that either patient paperwork 45 or radiographic images 25 have not been received by the radiology system 100, along with time indications, as shown. (The "hourglass" in the graphic indicates that the radiology system 100 is "waiting" for additional patient information.) Icons 170F and 170G indicate that both the radiographic image 25 and the patient paperwork 45 have been received, but no preliminary report 35 has been generated. Icons 170H, 170I, and 170J indicate that the preliminary report 35 has been generated, and additionally indicate the level of review (clinician only, clinician and department radiologist, and department radiologist only, respectively).

Patients for whom preliminary reports 35 have been generated and fully reviewed will be associated with the icon 170I. Since the work of the radiology system 100 is complete for these patients, their associated icons no longer change. For all other patients, their associated icon may change several times before the patient status is considered complete.

The matching function 58 within the central server 50 joins the radiographic images 25 with the patient paperwork 45, as soon as both are received into the radiology system 100. In some embodiments, the matching function 58 executes continuously, such that connections made between the two items of information 25 and 45 are nearly simultaneous to the receipt of the latter item. In other embodiments, the matching function 58 is executed periodically, such as every minute. In still other embodiments, the matching function 58 is executed each time an item of information is received into the radiology system 100, whether it be incoming radiographic images 25 or incoming patient paperwork 45.

Figure 11:
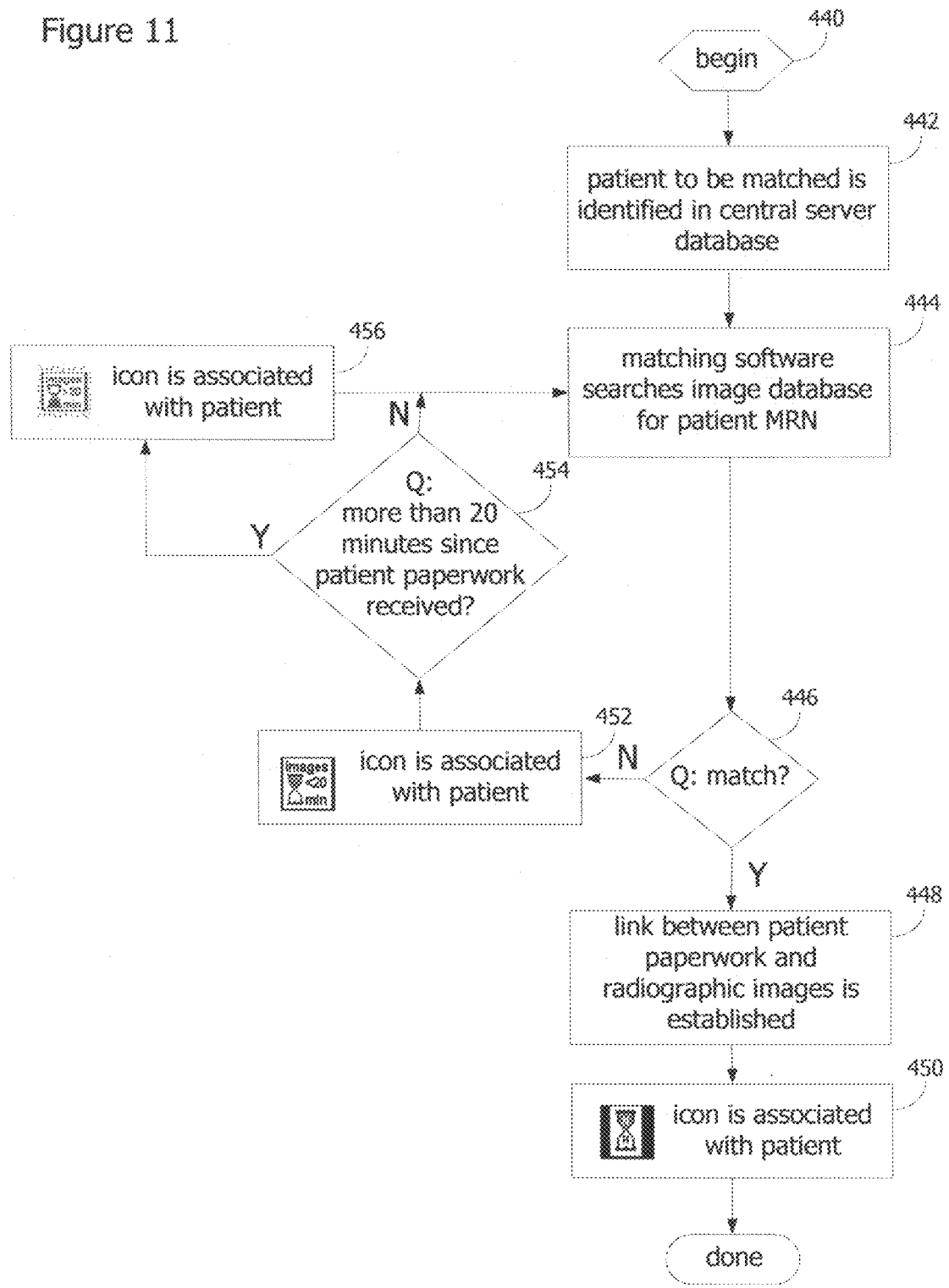
FIGS. 11 and 12 are flow diagrams illustrating the process for matching patient paperwork with radiographic images by the radiology system of FIG. 2, according to some embodiments.
Figure 12:
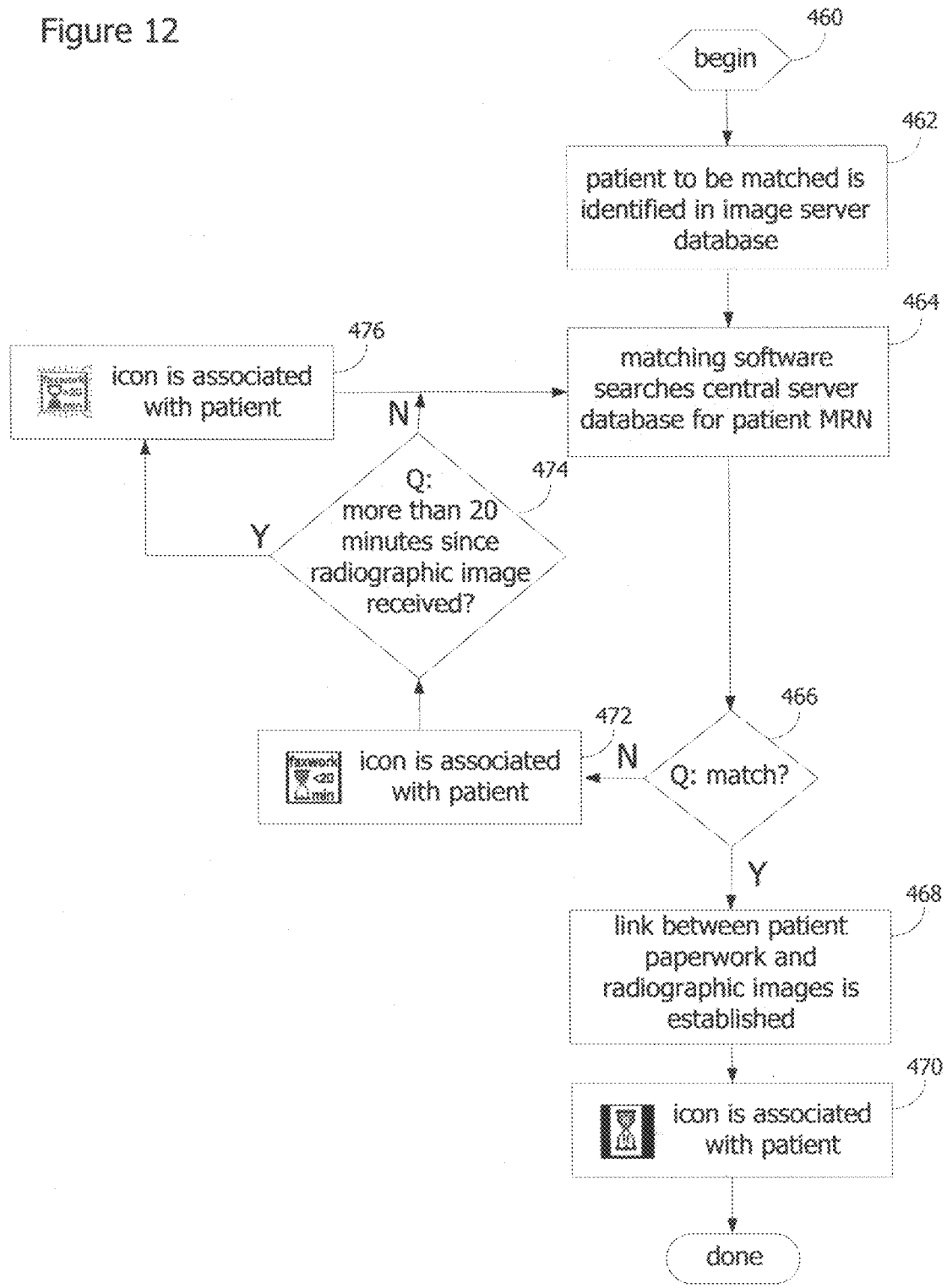

FIGS. 11 and 12 are flow diagrams describing a process for matching radiographic images 25 with patient paperwork 45, both of which are obtained by the radiology system 100 from a remote facility, according to some embodiments. Although the operations are depicted as occurring in a particular order, one or more operations may occur in a different sequence, as those of ordinary skill in the art will recognize, without departing from the spirit of the disclosure. In FIG. 11, a patient to be matched is identified from the central server database (based on patient paperwork 45 received), then the image server database is scanned for a match; in FIG. 12, a patient to be matched is identified from the image server database (based on radiographic image 25 received), then the central server database is scanned for a match.

In FIG. 11, a patient to be matched is identified in the central server database 52 (block 442), with the matching function 58 retrieving the MRN 30 of the patient. This identification may be made in a number of different ways. Patients whose status is complete (associated with icon 170I) may be passed over in the database 52, while patients with open status are identified for matching. The matching function 58 searches the image database 72 for a radiographic image 25 with an MRN 30 which is identical to the one retrieved from the central server database (block 444). Recall that the MRN of the radiographic image 25 is contained in its DICOM header 34 (see FIG. 4).

If a match is found (the "yes" prong of block 446), a link between the patient paperwork 45 on the central server database 52 and the radiographic image 25 on the image database 72 is made (block 448). This link may be in the form of a pointer, a stored address, or other linkage. Since both the radiographic image 25 and patient paperwork 45 for that patient has been matched, the icon 170E is associated with the patient (block 450). If, instead, no match is found (the "no" prong of block 446), the icon 170A, which indicates that the radiology system 100 is waiting for the radiographic images 25, is associated with the patient (block 452). If more than twenty minutes has transpired since the patient paperwork 45 was received by the radiology system 100 (the "yes" prong of block 454), the icon 170C is instead associated with the patient (block 456). Otherwise, the process is repeated until the radiographic image 25 associated with the patient is received into the radiology system 100.

In FIG. 12, a patient to be matched is identified in the image server database 72 (block 462), with the matching function 58 retrieving the MRN 30 of the patient. The matching function 58 searches the central server database 52 for a radiographic image 25 with an MRN 30 which is identical to the one retrieved from the image server database (block 464). Recall that the MRN of the patient paperwork 45 is contained in its PCS 94 (see FIG. 7A).

If a match is found (the "yes" prong of block 466), a link between the patient paperwork 45 on the central server database 52 and the radiographic image 25 on the image database 72 is made (block 468). Since both the radiographic image 25 and patient paperwork 45 for that patient has been matched, the icon 170E is associated with the patient (block 470). If, instead, no match is found (the "no" prong of block 466), the icon 170B, which indicates that the radiology system 100 is waiting for the patient paperwork 45, is associated with the patient (block 472). If more than twenty minutes has transpired since the radiographic image 25 was received by the radiology system 100 (the "yes" prong of block 474), the icon 170D is instead associated with the patient (block 456). Otherwise, the process is repeated until the patient paperwork 45 associated with the patient is received into the radiology system 100.

Radiology System User Interface

The radiology system 100 is accessible to users of the Worldwide web or other wide-area network. Users may be radiologists, clinicians, technicians, or other medical professionals who have previously registered with the radiology system 100 and been given a username and password. Users enter a predefined web address or uniform resource locator (URL), causing a web page to be displayed. The initial web page is essentially a logon screen for accessing the radiology system 100. Since the radiology system 100 is a private network, the user will be prompted to enter a username and password before access to the system is granted. (Other features, such as the ability to register for access, obtain password hints, and so on, may additionally be available on the initial logon screen.) Once the correct username and password are entered, a graphical user interface, such as the display interface 150 of FIG. 13, is presented to the user, allowing further access to the information collected by and produced for the radiology system 100.

FIG. 13 is a representation of a display interface 150 for accessing the radiology system 100 of FIG. 2, according to some embodiments. The display interface 150, generated by the user interface software 54 on the central server (FIG. 9), is a graphical user interface (GUI) visible on a web page. In some embodiments, the display interface 150 and a patient list 160 (FIG. 14) are simultaneously displayed on the web page.

The display interface 150 enables users of the radiology system 100 to access patient information that is stored thereon. Users make inquiries into the system, in the form of search queries, to obtain the desired patient information, which is presented in list form. (An example of a patient list 160 is depicted in FIG. 14, and is described in more detail, below.) The resulting patient information may be presented to the user in the form of a new web page, or may be presented along with the display interface 150, wherein the display interface 150 occupies a portion, but not all of the display window and the patient information occupies the remainder of the display window. The patient information may be complete, that is, including the preliminary report 35 generated by the radiologist, or the patient information may merely include patient information that has been obtained thus far by the radiology system 100, such as the radiographic image 25 or the patient paperwork 45. As soon as patient information is stored within the radiology system 100, the patient information may be available to the user upon inquiry.

At any given time, the system 100 may be storing patient information for a large number of patients in the databases 52 and 72 (FIG. 9). The display interface 150 thus provides a mechanism by which the patient information may be efficiently retrieved using a number of different search criteria, or filters, some of which are selectable by typing information into a field, and some of which are selectable using a mouse or other pointing device. A time filter 102, a modality filter 104, a date filter, 106, and a patient filter 108 are examples of filters visible on the display interface 150 and available to users of the radiology system 100.

The time filter 102 enables the user to select patient information based on a number of time criteria. In some embodiments, the time filter 102 includes the following criteria: since 4 p.m. C.S.T., last 48 hours, last week, last month, and all. The modality filter 104 enables the user to select patient information for patients obtaining a certain type of radiological image. In some embodiments, the modality filter 104 includes the following criteria: MRI, CAT scan, ultrasonography, nuclear medicine, and x-ray. Time and modality criteria are selectable by positioning a cursor on a radio button adjacent to the desired selection, clicking the mouse button (other pointing devices may be used in a similar fashion), then clicking on a search button 144.

The date filter 106 enables the user to select patient information obtained by the radiology system 100 between two dates entered by the user. The patient filter 108 enables the user to select patient information based on patient criteria. In some embodiments, the available patient criteria include first and last name, hospital, and MRN. The date and patient filters are selected by typing data directly into the available fields. One of the patient filter fields, "hospital," includes a pull-down menu of all medical facilities serviced by the radiology system 100.

The time filter 102, the modality filter 104, the date filter 106, and the patient filter 108 may be used together, if desired. Obtaining all MRI requests from a certain hospital during a two-day period is a valid search in which the user would simultaneously use the time filter 102 (or the date filter 106), the modality filter 104, and the patient filter 108. Once all search criteria are entered, the user selects the search button 144, at which point the user interface software 54 produces a patient list conforming to the search criteria. The display interface 150 thus offers an attractive, easy-to-use mechanism by which users of the radiology system 100 may readily obtain patient information.

In some embodiments, some patient information, in the form of a default patient list, is presented along with the display interface 150, without the user entering any search criteria. The default patient list may include information for all patients entered into the system in the last twenty-four hours, the last twenty patients entered into the system, or other criteria, as desired.

Some information is generated automatically on the display interface 150, based upon the username and password entered. Such information is shown in FIG. 13 in italics. User information 110, status information 112, hours of operation 114, and on-call information 116, are among the fields entered automatically by the user interface software 54. Automatically generated information is not limited to the format and content featured in FIG. 13. Any information obtainable from the DICOM header of the radiographic image 25 (FIG. 4), as well as registration information obtained from the user, may be presented automatically as part of the display interface 150. In some embodiments, user information 110 includes the user name, user email address, user logon level, and hospital associated with the user. The "level" field specifies the access level to the radiology system 100 available to the user. The user level may be used to limit access to different parts of the radiology system 100. User level may also be used to limit access to patient information for a particular hospital.

A number of other functions in the display interface 150 may be available to all users or to a limited group of users, as desired. Administrative 118, statistics 120, print latest reports 122, preliminary report 124, patient demographics 126, hospital code/MRN 128, sent/posted/turnaround 130, clinician review 132, radiologist review 134, F/U 136, IC 138, on-call hospitals 140 and change department radiologist on call 142 are among the additional selectable functions of the display interface 150 to give users access to patient information stored on the radiology system 100. Each of these functions is accessible by clicking the desired function with a mouse. The administrative function 118 and statistics function 120 are described more detail, below.

Figure 15:
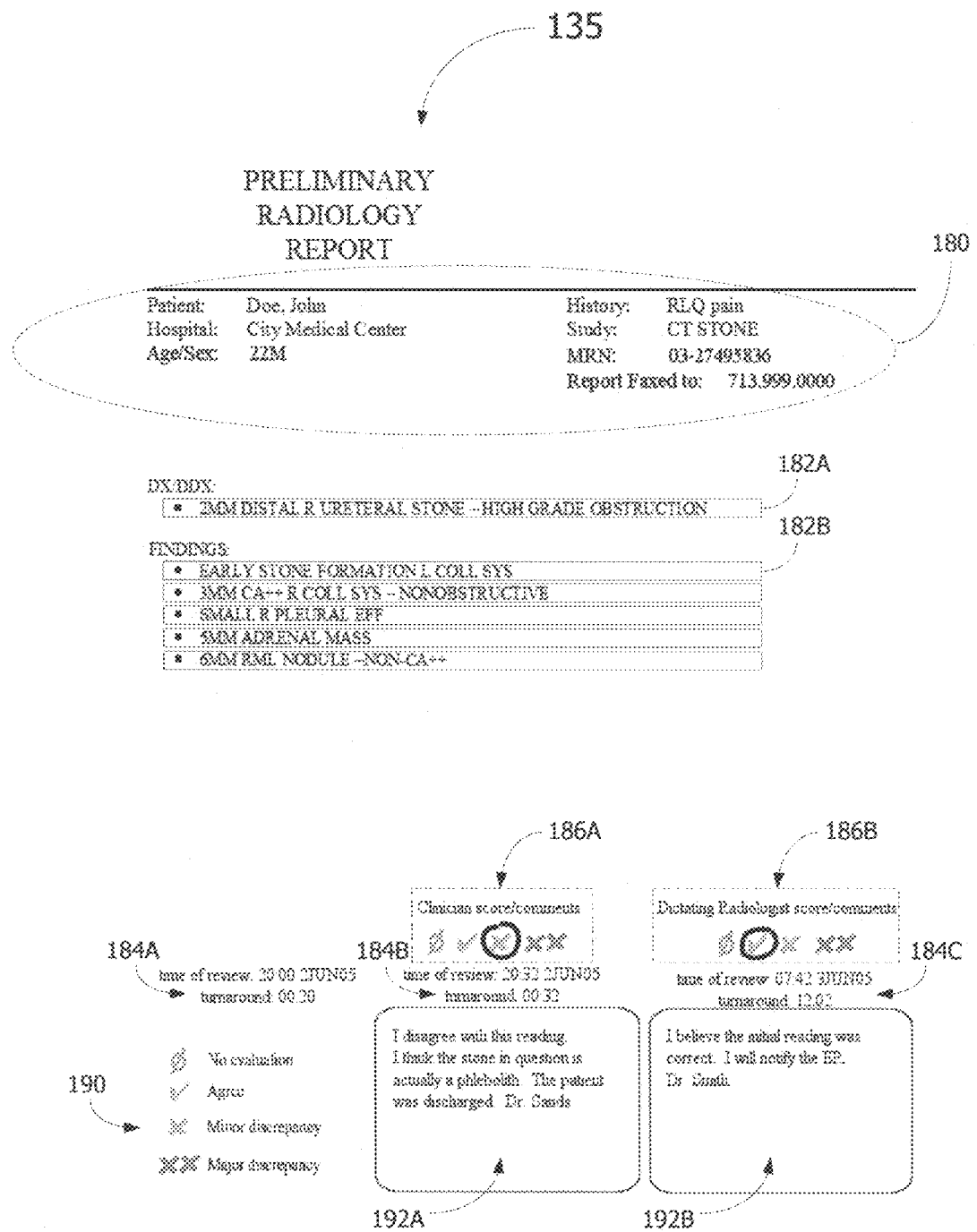
FIG. 15 is a sample of a preliminary report generated in the system of FIG. 2, according to some embodiments.

The print latest reports 122, shown in FIG. 11 as "print all reports from the last 24 hours," enables the user to retrieve and print all patient information that have been generated within the last twenty-four hours. (Other time periods may be specified, as desired). The preliminary report function 124 causes a new web page to be displayed, which includes a template of a preliminary report 35. The preliminary report 35 is discussed further below, and a sample preliminary report is depicted in FIG. 15. The clinician review function 132 enables the clinician to review the preliminary report 45. The radiologist review function 134 enables the radiologist to review the preliminary report. (A sample preliminary report 45 is shown in FIG. 15 and is discussed in more detail below.)

The F/U 136 function, or follow-up function, enables the radiologist to review the preliminary report 45 after the clinician has posted a review. The IC 138 function, or interesting case function, enables the radiologist to tag the preliminary report 45 as interesting, such as where an unusual patient malady is present in the radiographic image 25. The IC 138 function enables subsequent statistical analysis of radiographic images 25 (using the statistics 120 function) to include those cases deemed interesting.

The on-call hospitals 140 function provides a list of on-call hospitals available to the radiology system 100. The change department radiologist on call 142 function enables the on-call radiologist to be changed.

When the user first accesses the display interface 150 (by entering username and password), the radiology system 100 additionally presents a patient list 160, as depicted in FIG. 14, according to some embodiments. The web-based display page is thus split to allow both the display interface 150 and the patient list 160 to simultaneously be visible to the user. The patient list 160 is produced as a result of the patient filter 108 defaulting to all patients and all hospitals for which the user has authorized access, for a predetermined time period. In some embodiments, the patient list 160 defaults to providing all patients entered into the radiology system 100 since 4 p.m. Central Standard Time.

In the sample patient list 160 of FIG. 14, all patient names and other included data are fictional. An icon 170 is associated with each of the six patients in the list. The icons 170 indicate that preliminary reports 35 have been prepared for Fred Higgins (reviewed by department radiologist only) and Karen Johnson (clinician and department radiologist have reviewed); preliminary reports 35 are pending for Mary Douglas and Sam Turner (as both radiographic images 25 and patient paperwork 45 have been received for each patient); for patient James Brown, patient paperwork 45 has been received but no radiographic images 25 (and, more than twenty minutes has passed since the patient paperwork was received); for patient Rosemary Peterson, radiographic images 25 have been received but no patient paperwork 45 (but, less than twenty minutes have passed since receiving the radiographic images). Without looking at any other information in the patient list 160, a substantial amount of information is conveyed using the icons 170.

In addition to providing patient names and current status (via the icons 170), the patient list 160 includes an image requested field 162 and a patient symptoms field 164 (shown in FIG. 14 beneath the patient name). The image requested field 162 indicates the type of radiographic study that was ordered for the patient. The field 162 is automatically entered in the patient list 160 when the radiographic image 25 for that patient becomes available. Thus, for Rosemary Peterson, the image requested field 162 is blank, since no radiographic image 25 has been sent to the radiology system 100 for her. The patient symptoms field 164 indicates the symptoms reported by the patient. Thus, for James Brown, for whom patient paperwork 45 has not yet been received by the radiology system 100, the patient symptoms field 164 is blank.

For those patients whose preliminary report 35 has been generated, the patient list 160 also includes a preliminary report field 166. The preliminary report field 166 is a hyperlink. Thus, the user may click on the preliminary report field 166, which causes a web page with the patient's preliminary report to be displayed. The patient list 160 also includes a hospital code field 168, a patient MRN field 170, and a report completion field 172. The report completion field 172 includes three entries: the time and date at which the radiographic images 25 and patient paperwork 45 are received by the radiology system 100, the time and date at which the preliminary report 35 is completed, and the difference between the two times. (Further, the name of the radiologist who produced the preliminary report is indicated in the report completion field 172.)

The information available from the patient list 160 may be presented in a variety of formats. The icons 170 provide quick indication of patient status, although more detailed information is also made available from the patient list 160. Further, the patient list 160 provides access to the preliminary report 35 via a hyper-link. The patient list 160 may include other features not depicted in FIG. 15, such as providing the user with the ability to fax preliminary reports to a location once available.

As explained above, the patient list 160 may be presented simultaneously with the display interface 150, or may be presented as a search result, upon receiving inquiry by the user. The patient demographics 126, hospital code/MRN 128, and sent/posted/turnaround 130 selections of the display interface 150 (FIG. 13) enable the user to change order at which patients are presented in the patient list 160. For example, the user may prefer to see the patient information according to the hospital servicing the patients. The user then selects the hospital code/MRN function 128, which causes the patient list 160 to present patient information from a first hospital, then patient information from a second hospital, and so on.

If the user selects the patient demographics function 126, the patient list 160 is ordered according to patient information, such as last name. Using this function, the patient list 160 may be presented in alphabetical order, as one example. Where the user selects the sent/posted/turnaround function 130, the patient information is ordered according to the time of processing. Where the user selects the sent/posted/turnaround function 130 (FIG. 13), the patients are listed in the patient list 160 is presented according to information provided in the report completion field 172 (FIG. 14).

In FIG. 15, an example of a preliminary report 135 generated by the radiology system 100 is depicted, according to some embodiments. A portion 180, shown at the top of the preliminary report 135, is generated automatically by the radiology system 100 by extracting patient information from the DICOM header 34 of the radiographic image 25.

The preliminary report 135 also includes a diagnosis field 182A (shown as dx/ddx, shorthand for "diagnosis/differential diagnosis") and a findings field 182B. Both fields are completed as the radiologist reviews the radiographic image 25. The diagnosis field 182A includes the radiologist's diagnosis of the patient. The findings field 182B includes any and all observations made by the radiologist. In FIG. 15, the findings field 182B is several lines long, allowing for multiple entries to be made. Since the radiologist may observe multiple findings during review of the radiographic image 25, the diagnosis field 182A typically includes a single finding that is deemed most important.

The preliminary report 135 is completed by the on-call radiologist, at which point the status icon for the patient will change to the icon 170J (preliminary report reviewed by department radiologist only). Then, the preliminary report is reviewed by a clinician, at which point the status icon for the patient will again change to the icon 170H (preliminary report reviewed by clinician only). Finally, the preliminary report is reviewed by a second radiologist, at which point the status icon again changes to the icon 170I (preliminary report reviewed by clinician and department radiologist). (The on-call radiologist, clinician, and department radiologist are referred to herein as reviewing entities.) When the icon associated with the patient is the icon 170I, the patient review is complete.

As shown in FIG. 15, the preliminary report 135 includes fields to facilitate processing of the patient radiographic image 25 by each of the reviewing entities. Timestamp fields 184A, 184B, and 184C are completed automatically by the radiology system 100 when the radiologist, clinician, and department radiologist, respectively, complete their review of the radiographic image 25. A scoring system 190 enables each reviewing entity to score the diagnosis made by the previous reviewing entity. The scoring system 190, which includes both textual information and graphics, provides selections for "no evaluation," "agree," "minor discrepancy," and "major discrepancy."

In some embodiments, a selection of keyboard keys are programmed to automatically score the preliminary report 35. Thus, for example, the F6 key may be programmed to select "agree," the F7 key may programmed to select "minor discrepancy," and the F8 key may be programmed to select "major discrepancy." This further enhances the ability of the on-call radiologist, clinician, and department radiologist to quickly score the preliminary report using simple keystrokes that are easy to remember.

A clinician scoring field 186A enables the clinician to score the diagnosis made by the on-call radiologist by clicking on a graphic; an associated comment field 192A allows the clinician to further specify the reason(s) for the score. The time stamp field 184B is automatically completed once the clinician scoring field 186A and comment field 192A are completed. Likewise, a department radiologist scoring field 186B enables the hospital or department radiologist to score the diagnosis made by the clinician by clicking on a graphic; an associated comment field 192B enables the department radiologist to further comment on the score made. The time stamp field 184C is automatically completed once the department radiologist completes the department radiologist scoring field 186B and associated comment field 192B.

In some embodiments, the score given by the department radiologist is with respect to the diagnosis of the original on-call radiologist, not based on the clinician review. Thus, in the example preliminary report 135 of FIG. 15, the clinician indicated a "minor discrepancy" with the radiologist's diagnosis, and provide additional statements in the comment field 192A. The department radiologist, who believed the original diagnosis to be correct, so indicated by selecting "agree" in the department radiologist scoring field 186B, and also provided additional statements in the comment field 192B.

While the scoring fields 186A and 186B may be completed by selecting the desired graphic using a mouse or other pointing device, the other fields in the preliminary report 135 may be completed by selecting the desired field, then typing in the fields. In some embodiments, the diagnosis field 182A, the findings field 182B, and the comment fields 192A and 192B may be completed using oral dictation. Recall that the optional dictation server 80 may generate dictation scripts 84 to the preliminary report (see FIG. 6). This provides the reviewing entities with multiple facile options for quickly completing the preliminary report.

Timing Function

Returning to FIG. 9, the radiology system 100 also includes a timing function 66, according to some embodiments. The timing function 66 keeps track of the start, end, and duration of various activities within the radiology system 100, including the time differential between receiving patient paperwork 45 and radiographic images 25, completed studies, and review of studies. Recall that the patient list 160 includes a report completion field 172 (FIG. 14). The contents of the report completion field 172 are obtained by the timing function 66.

Remote Facility

As discussed above, the radiology system 100 provides a mechanism by which radiographic images 25 and patient paperwork 45 for a particular patient may be obtained and matched up efficiently, so that the on-call radiologist is able to quickly produce the preliminary report 35. Several parties may be involved in the process, including the physician who makes the original radiology request, the radiologist technician who scans the patient, the on-call radiologist who produces the preliminary report, the clinician who reviews the preliminary report, and the department radiologist who provides final review of the preliminary report. Although these individuals have traditionally been physically present at the remote facility, the radiology system 100 makes it possible for each of the individuals to be physically separated from one another, and from the radiology system itself. The following discussion describes the radiology system 100 from the perspective of the individuals who use the radiology system 100, whether at the remote facility or not.

Radiologist Technician

Figure 16:
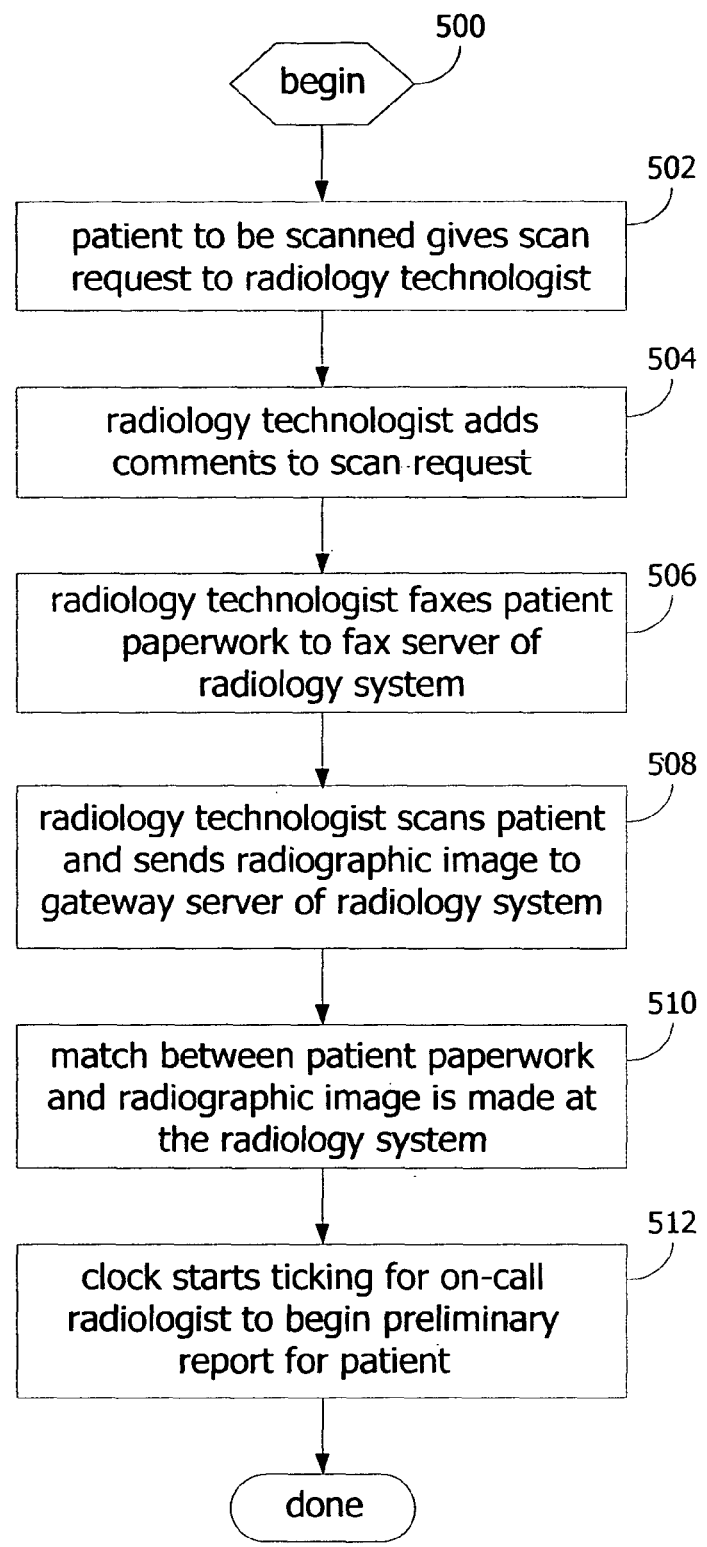
FIG. 16 is a flow diagram of the workflow process for a radiologist technician at the remote facility using the radiology system of FIG. 2, according to some embodiments.

FIG. 16 is a flow diagram of the workflow process for the radiologist technician, according to some embodiments. The radiologist technician is the person who scans the patients at the remote facility. When the radiologist technician first sees the patient, the patient (or attending nurse) gives a scan request to the radiologist technician (block 502). The scan request may be a formal document with a predefined format or a simple directive received from the ordering physician. Based on the personal interaction of the radiology technician with the patient, the radiology technician may optionally add some information to the scan request. The scan request plus the additional information form the patient paperwork 45 referred to herein. The radiology technologist faxes the patient paperwork 45 to the fax server 90 of the radiology system 100 (block 506).

Once the fax has been received to the fax server 90, anybody logging into the radiology system 100 would be able to obtain information about the patient, whether part of the default patient list displayed with the display interface 150 or part of a patient list produced as the result of an inquiry. The radiology technician scans the patient according to the initial request, and then sends the radiographic image 25 to the gateway server 60 of the radiology system 100 (block 508). In some embodiments, the radiographic image 25 is transmitted to the radiology system 100 using electronic mail. (The operations of blocks 506 and 508 may be reversed, such that the radiographic images 25 are sent before the patient paperwork 45.)

Since the matching function 58 at the central server 50 is continuously checking for matches between radiographic images 25 and patient paperwork 45, a match between the two is made in the radiology system 100 (block 510). Once the match is made, a dedicated timer is initiated for that patient by way of the timing function 66 (FIG. 9). The timer keeps track of the delay between receipt of information and subsequent production of the preliminary report 35 by the on-call radiologist (block 512).

At any point in the workflow process of FIG. 16, the radiology technologist (or any other individual who has access) may log into the radiology system 100 and inquire as to the status of the patient. Status icons 170, such as those depicted in FIG. 10, provide visual indication of the patient status. These icons are likely to change for each patient until the preliminary report 35 is completed and reviewed. Once the radiologist technician has completed the scan and sent both the radiographic image 25 and the patient paperwork 45 to the radiology system 100, the patient status should not indicate that incoming information is still pending (e.g., icons 170A, 170B, 170C, or 170D). If one of the pending icons is displayed for the patient, the radiologist technician can quickly identify this from the patient list and resend either the patient paperwork 45 or the radiographic image 25.

On-Call Radiologist

Figure 17:
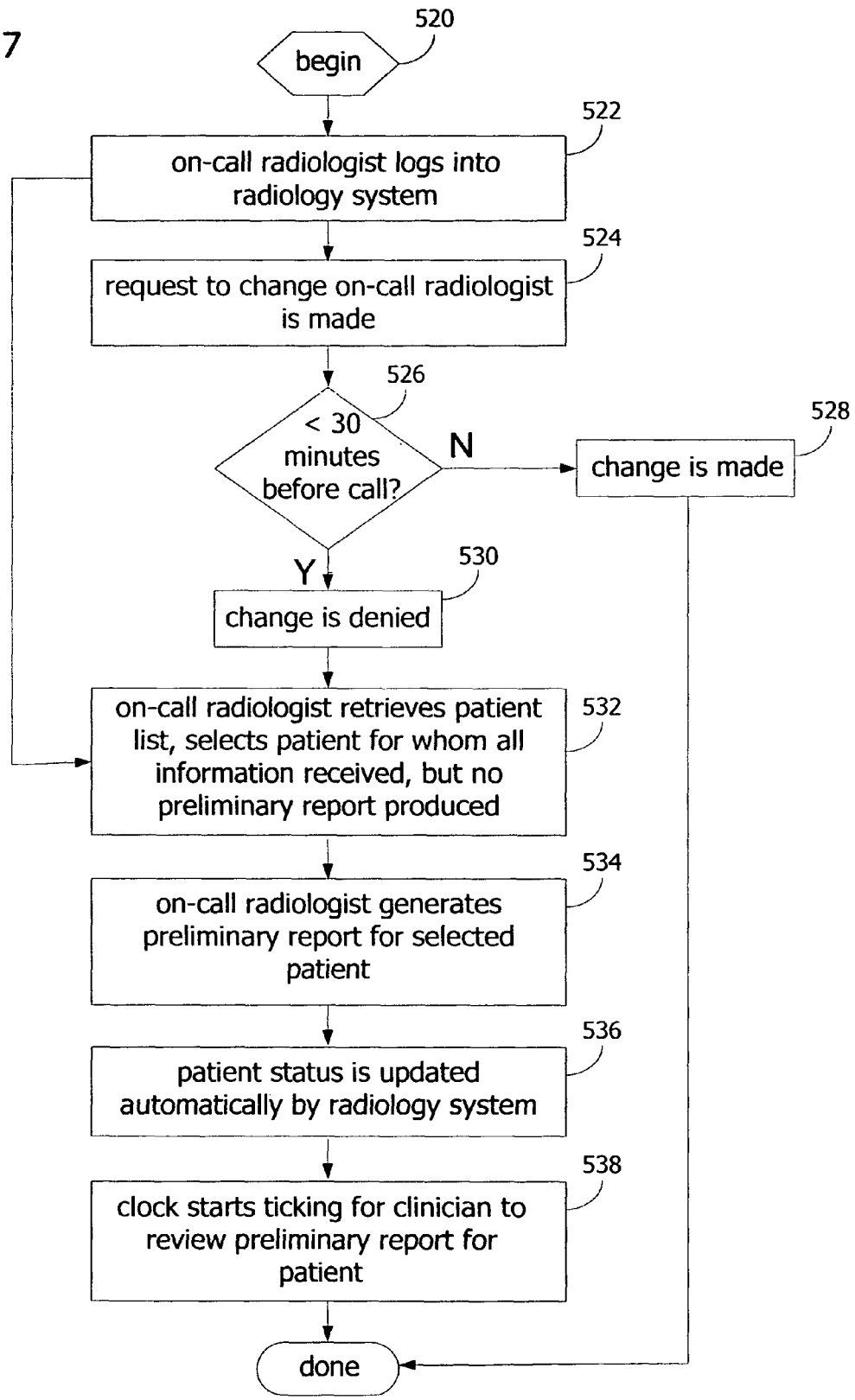
FIG. 17 is a flow diagram of the workflow process for an on-call radiologist using the radiology system of FIG. 2, according to some embodiments.

FIG. 17 is a flow diagram of the workflow process for the on-call radiologist, according to some embodiments. The on-call radiologist is the individual who is expected to produce the preliminary report 35. The radiology system 100 makes the patient paperwork 45 and radiographic images 25 for each patient available to enable the on-call radiologist to produce the preliminary report 35 in a timely manner.

The on-call radiologist logs into the radiology system 100, as described above (block 522). In some embodiments, the individual who is designated as the on-call radiologist may optionally change the on-call designation by logging into the system and making a change request, as long as the change is timely (e.g., not less than thirty minutes prior to commencement of call). (Permission to make such changes may be restricted to certain specified individuals, as desired.) Where the on-call radiologist makes an on-call change request (block 524), the radiology system 100 ascertains whether the request is made within the designated time period (block 526), in this case, thirty minutes. If not, the change to the on-call radiologist is deemed timely and is thus made (block 528). If the request is made within the designated time period, the change to the on-call radiologist is deemed untimely and is thus denied (block 530). Where the on-call designation is changed, the on-call radiologist making the request is likely to log out of the radiology system 100.

Where the on-call designation is denied, or where no designation request was made, the on-call radiologist retrieves the patient list 160, whether the default patient list 160 presented along with the display interface 150 or a patient list 160 produced as a result of an inquiry. From the patient list 160, the on-call radiologist selects a patient for whom radiographic image 25 and patient paperwork 45 have been obtained, but for whom no preliminary report has been produced (block 532), i.e., a patient whose status icon is icon 170F or 170G (FIG. 10).

With the assistance of the patient paperwork 45, the on-call radiologist reviews the radiographic image 25 for the patient and produces a preliminary report (block 534). A blank preliminary report 35 may be presented automatically by the radiology system 100 by selecting the preliminary report button 124 in the display interface 150 (FIG. 13). The diagnosis 182A and findings fields 182B may be completed by typing words or using dictation. The radiology system 100 automatically updates the patient status icon (block 536), to indicate that a preliminary report has been completed (icon 170G). By way of the timing function 66, a timer is initiated, which keeps track of the delay between on-call radiologist review and subsequent clinician review of the preliminary report 35 (block 538).

Clinician

Figure 18:
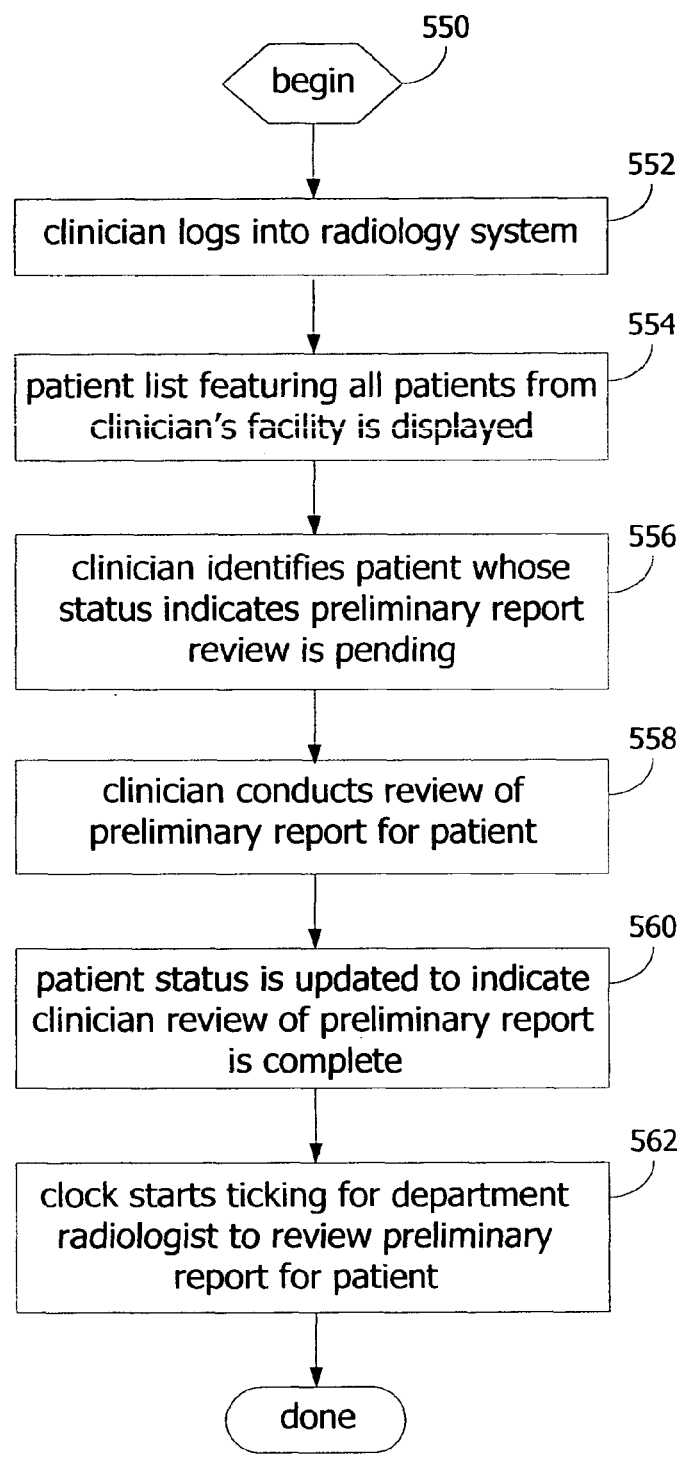
FIG. 18 is a flow diagram of the workflow process for a clinician using the radiology system of FIG. 2, according to some embodiments.

FIG. 18 is a flow diagram of the workflow process for the clinician, according to some embodiments. The clinician is the individual who reviews the preliminary report 35 following its production. The clinician may be an emergency room physician or other doctor working at the remote facility.

The clinician logs into the radiology system 100, as described above (block 552). Along with the display interface 150, the patient list 160 is presented to the display. The patient list 160 features all patients from the clinician's facility, such as a hospital (block 554). Looking at the status icons 170, the clinician is able to identify one or more patients for whom first review of the preliminary report 35 is pending (block 556). Accordingly, the clinician selects one of the patients in the patient list 160, selects the preliminary report field 166 for that patient, and reviews the preliminary report 35 (block 558). The clinician scores the preliminary report 35 by selecting one of the score options in the clinician scoring field 186A and providing comments in the associated comment field 192A (FIG. 15). Entries in the clinician scoring field 186A may be made by selecting with a mouse or other pointing device, or the clinician's keyboard may be programmed to accept designated keystrokes, as described above. The comments may be typed into the comment field 192A or they may be dictated, as desired. (If the clinician selects "agree" in the scoring field, the comment field 192A may be left blank.)

Once the clinician review is complete, the patient status is automatically updated to so indicate (block 560), such as using icon 170H. By way of the timing function 66, a timer is initiated, which keeps track of the delay between clinician review and subsequent department radiologist review of the preliminary report 35 (block 562).

Department Radiologist

Figure 19:
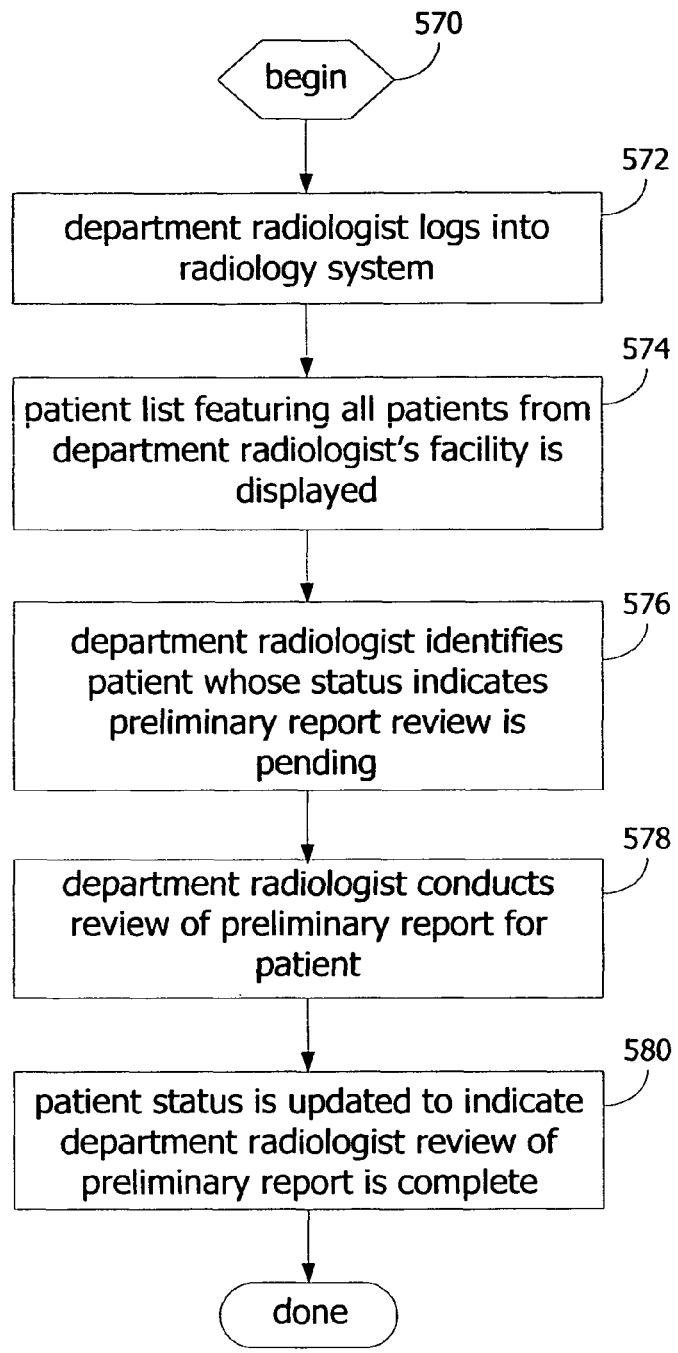
FIG. 19 is a flow diagram of the workflow process for a department radiologist using the radiology system of FIG. 2, according to some embodiments.

FIG. 19 is a flow diagram of the workflow process for the department radiologist, according to some embodiments. The department radiologist is the individual who finally reviews the preliminary report 35 before it is returned to the ordering physician. Preliminary reports are typically reviewed by both a clinician and a department radiologist before being "signed off" as complete. The radiology system 100 facilitates this process so that the preliminary report may be completed in as timely a manner as possible.

The department radiologist logs into the radiology system 100, as described above (block 572). Along with the display interface 150, the patient list 160 is presented to the display. The patient list 160 features all patients from the department radiologist's facility, such as a hospital (block 574). Looking at the status icons 170, the department radiologist is able to identify one or more patients for whom second review of the preliminary report 35 is pending (block 576). Accordingly, the clinician selects one of the patients in the patient list 160, selects the preliminary report field 166 for that patient, and reviews the preliminary report 35 (block 578). The department radiologist scores the preliminary report 35 by selecting one of the score options in the department radiologist scoring field 186B and provide comments in the associated comment field 192B (FIG. 15). Entries in the department radiologist scoring field 186B may be made by selecting with a mouse or other pointing device, or the department radiologist's keyboard may be programmed to accept designated keystrokes, as described above. The comments may be typed into the comment field 192B or they may be dictated, as desired. (If the department radiologist selects "agree" in the scoring field 186B, the comment field 192B may be left blank if the clinician scoring field 186A also specifies the "agree" selection.)

Once the department radiologist review is complete, the patient status is automatically updated to so indicate (block 580), such as using icon 170I. It is possible that the department radiologist conducts a review of the preliminary report 35 prior to when the clinician does so. If that is the case, the patient status following review by the department radiologist will indicate that department radiologist review only has been conducted (e.g., icon 170J).

Administration

Returning to FIG. 9, the radiology system 100 includes an administrative function 56, according to some embodiments. The administrative function 56 is preferably available to a small number of individuals (hereinafter, administrators) using the radiology system 100. The administrative function 56 allows administrators to add users, manage users, search for a particular user, edit the on-call schedule, manage records, add/remove hospitals, manage department radiologists' schedules, bill hospitals, add fax numbers at hospitals, and manage fax numbers, to name a few available functions. In some embodiments, information entered by administrators is interactive throughout the radiology system 100, so that double entry of information may be avoided. After logging into the radiology system 100, the administrator may access the available administrative functions by selecting the administrative function 118 (FIG. 13) that is available in the display interface 150.

Statistics Rendering

The radiology system 100 provides a mechanism for generating statistics, according to some embodiments. Statistics may be obtained, for a given date interval and choice of medical facility, such as the total number of patient studies obtained, the number of studies performed in each modality, the total hours of service provided, the total cost, the average number of cases per shift, the average number of cases per hour, the percentaged agreement on studies scored by both the clinician and radiologist, the average turnaround time per study, the percentage of delinquent studies, and the percentage breakdown of scores from both the clinician and department radiologist. After logging into the radiology system 100, users may access the available statistics functions by selecting the statistics function 120 (FIG. 13) that is available in the display interface 150.

Figure 20:
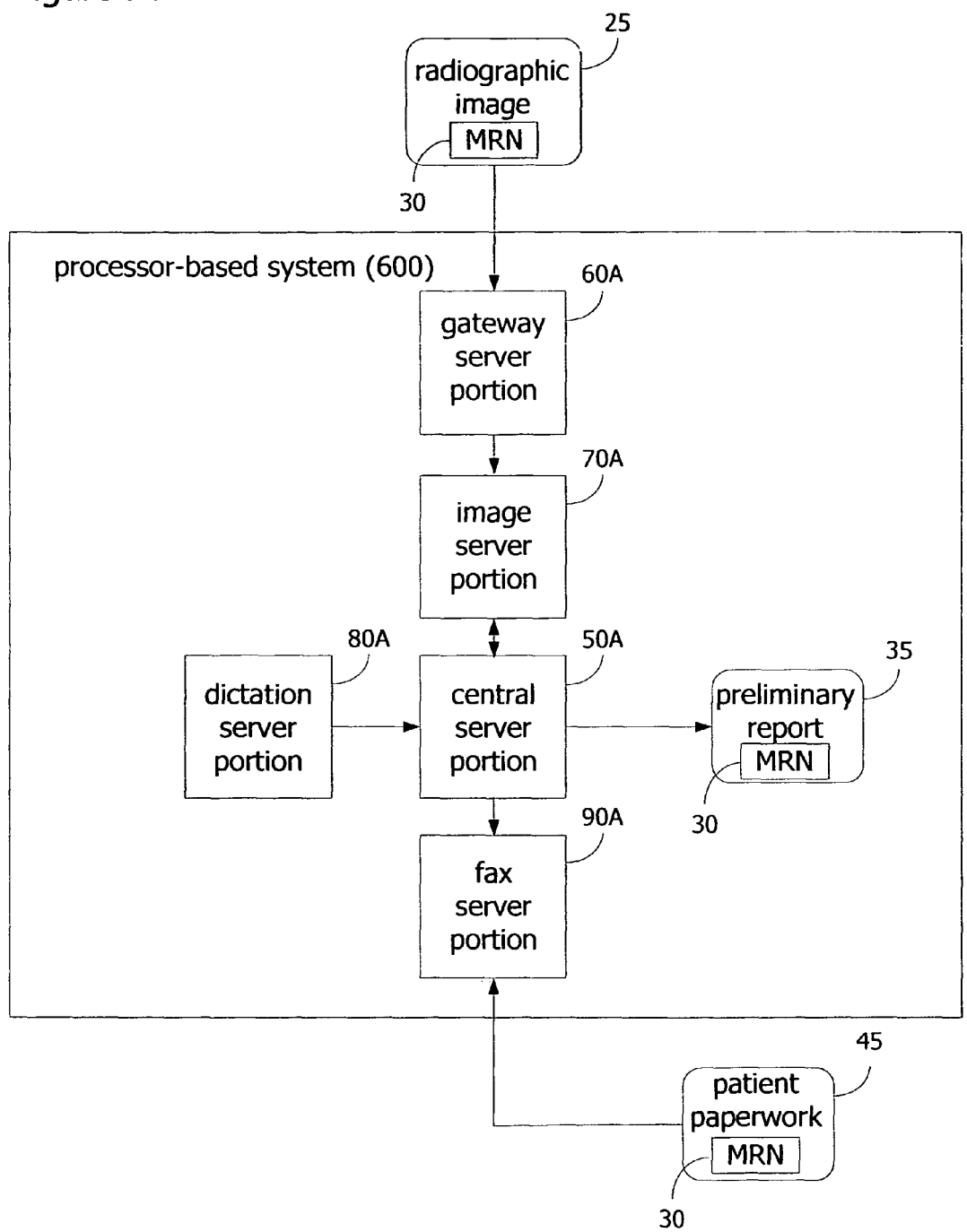
FIG. 20 is a block diagram of a processor-based system using the radiology system of FIG. 2, according to some embodiments.

FIG. 20 is a block diagram of a processor-based system 600 using the radiology system 100 of FIG. 2, according to some embodiments. The servers 50, 60, 70, 80, and 90 of FIG. 2 may be distinct processor-based systems, such as servers, personal computers, laptop computers, and the like. However, the various functions that make up the radiology system 100 may reside on a single processor-based system, such as the processor-based system 600 depicted in FIG. 20. The radiographic image 25 is received into a gateway server portion 60A of the processor-based system 600, and is then stored on an image server portion 70A. The patient paperwork 45 may be received across a telephone line into a fax server portion 90A, and stored on a central server portion 50A. An optional dictation server portion 80A may include voice recognition software to facilitate the production of the preliminary report 35.

While the invention has been described with respect to a limited number of embodiments, those skilled in the art will appreciate numerous modifications and variations therefrom. It is intended that the appended claims cover all such modifications and variations as fall within the true spirit and scope of the invention.

I claim:

1. A radiology system, comprising:
an image server coupled to a network, the image server comprising an image database, wherein the image server receives a radiographic image of a patient from across the network and stores the radiographic image in the image database;
a central server comprising:
a database, wherein the central server receives patient paperwork and stores the patient paperwork in the database;
matching software, wherein the matching software couples the patient paperwork in the database with the radiographic image in the image database based on the medical record number of the patient; and
timing software, wherein the timing software associates one of a plurality of status icons with each patient, the associated status icon being based on receipt of the radiographic image, receipt of patient paperwork, generation of a preliminary report, and/or review of the preliminary report, and the associated icon for each patient changes as the patient status changes, wherein the timing software further determines:
a first time associated with receipt of the patient paperwork of the patient, the first time being associated with a first status icon;
a second time associated with receipt of the radiographic image of the patient, the second time being associated with a second status icon; and
a third time associated with the generation of the preliminary report of the patient, the third time being associated with a third status icon; and
a web-based user interface comprising a preliminary report template, the preliminary report template comprising a plurality of fields, the plurality of fields comprising a diagnosis field, a findings field, and a scoring system, wherein the template is saved as the preliminary report once the diagnosis field and the findings field are completed, and the scoring system enables a user to denote, either textually, graphically, or both, agreement or disagreement with the original generation of the preliminary report;

wherein the user of the radiology system views the radiographic image and the patient paperwork and enters information in the plurality of fields of the preliminary report template to produce the preliminary report for the patient.

2. The radiology system of claim 1, further comprising:
a fax server coupled to a telephone line, wherein the fax server receives the patient paperwork transmitted across the telephone line and sends the patient paperwork to the database.

3. The radiology system of claim 2, wherein the patient paperwork is transmitted across the telephone line using a predefined code sequence, the predefined code sequence comprising:
a fax server access number;
a medical facility code to identify the medical facility from which the patient paperwork came, wherein the patient paperwork is thereafter associated with the medical facility; and
all or part of a patient medical record number, wherein the patient medical record number is a unique number associated with the patient whose patient paperwork is being faxed.

4. The radiology system of claim 3, the fax server further comprising:
translation software, wherein the translation software coverts the patient paperwork into a predefined format before the patient paperwork is stored in the database.

5. The radiology system of claim 1, further comprising:
a gateway server comprising decompression software, wherein the radiographic image is transmitted across the network in compressed form, received into the gateway server, and decompressed by the decompression software before being stored in the image database.

6. The radiology system of claim 1, further comprising:
a dictation server comprising voice recognition software, wherein the user of the radiology system generates dictation scripts using the voice recognition software and the dictation scripts populate the plurality of fields of the preliminary report template.

7. The radiology system of claim 1, the image server further comprising:
an image viewer, wherein the image viewer:
reads a header on the radiographic image;
extracts a medical record number of the patient from the header'
generates a health level seven message including the medical record number of the patient; and
transmits the health level seven message to the central server.

8. The radiology system of claim 1, wherein the matching software associates one of the status icons with the patient based on whether the radiographic image, patient paperwork, or both, are found.

9. The radiology system of claim 1, wherein the timing software further determines:
a fourth time associated with a first review of the preliminary report of the patient, the fourth time being associated with a fourth status icon; and
a fifth time associated with a second review of the preliminary report of the patient, the fifth time being associated with a fifth status icon.

10. The radiology system of claim 1, further comprising:
a default patient list comprising a plurality of patients, the plurality of patients being organized according to predetermined criteria, wherein each patient in the default patient list has an associated status icon; and
an interactive information display viewable from a web page, the interactive information display comprising a search engine interface, the search engine interface enabling the user to generate a user-specific patient list;
wherein the default patient list and interactive information display are presented as the user logs into the radiology system.

11. The radiology system of claim 10, wherein the user-specific patient list is based on one or more values entered in one or more filters in the search engine interface, wherein one of the one or more filters is selected from a group consisting of time filter, modality filter, date filter, and patient filter.

12. The radiology system of claim 10, the default patient list further comprising:
a hyperlink to the preliminary report of each patient whose preliminary report has been generated.

13. The radiology system of claim 1, wherein the status icon of the patient is selected from a group consisting of:
patient paperwork received, but no radiographic image received, less than twenty minutes;
patient paperwork received, but no radiographic image received, more than twenty minutes;
radiographic image received, but no patient paperwork received, less than twenty minutes;
radiographic image received, but no patient paperwork received, more than twenty minutes;
patient paperwork received, radiographic image received, but no preliminary report generated, less than twenty minutes;
patient paperwork received, radiographic image received, but no preliminary report generated, more than twenty minutes;
preliminary report generated, but not reviewed;
preliminary report generated, reviewed by clinician only;
preliminary report generated, reviewed by department radiologist only; and
preliminary report generated, reviewed by clinician and department radiologist.

14. The radiology system of claim 1, the preliminary report template further comprising:
the diagnosis field, wherein the user enters a diagnosis of the patient after reviewing the radiographic image and the patient paperwork; and
the finding field, wherein the user enters findings of the patient after reviewing the radiographic image and the patient paperwork;
wherein the diagnosis field and the findings field are completed in the preliminary report template and saved, producing the preliminary report of the patient.

15. The radiology system of claim 14, the preliminary report of the patient further comprising:
a clinician scoring field and a department radiologist scoring field, wherein the clinician scoring field and department radiologist scoring field are completed using a predefined scoring system;
an clinician comment field associated with the clinician scoring field; and
a department radiologist comment field associated with the department radiologist scoring field.

16. A method, comprising:
retrieving a radiographic image for a patient, the radiographic image including a medical record number of the patient, wherein the radiographic image is stored on an image server of a computer processor-based system;
retrieving patient paperwork for the patient, the patient paperwork being transmitted along with the medial record number of the patient, wherein the patient paperwork is stored on a central server of the computer processor-based system;
providing a web-based interface accessible to a user, the web-based interface comprising a patient name, medical record number, and status of the patient, the status of the patient being indicated by one or more of the following status icons:
a first status icon indicating when the patient paperwork has been retrieved;
a second status icon indicating when the radiographic image has been retrieved; and
a third status icon indicating when the preliminary report has been generated;
wherein the status and associated status icon of the patient is changed when the radiographic image is retrieved, the patient paperwork is retrieved, or the preliminary report is generated;
generating a preliminary report based on the radiographic image and the patient paperwork, the preliminary report comprising a first timestamp field indicating a first time of completion of the preliminary report;
reviewing the preliminary report by a reviewing entity, the preliminary report further comprising a second timestamp field indicating a second time of review of the preliminary report; and
providing a template of the preliminary report to the web-based interface, the template including a diagnosis field, a findings field, and a scoring system, wherein the template is saved as the preliminary report of the patient once the diagnosis field and the findings field are completed, and the scoring system enables the reviewing entity to denote either textually, graphically, or both agreement or disagreement with the original generation of the preliminary report;
wherein the preliminary report is generated when the status of the patient indicates that both the radiographic image and the patient paperwork have been received by the second processor-based system.

17. The method of claim 16, further comprising:
decompressing the radiographic image prior to storage on the image server of the processor-based system.

18. The method of claim 17, further comprising:
converting the patient paperwork to a preferred format before storing the patient paperwork on the central server of the second processor-based system.

19. The method of claim 16, further comprising:
matching the patient paperwork of the patient with the radiographic image of the patient, the medical record number of the radiographic image being identical to the medical record number transmitted with the patient paperwork.

20. The method of claim 16, further comprising:
displaying a patient list in the web-based interface, the patient list comprising a subset of all patients whose radiographic images have been stored on the image server of the processor-based system or whose patient paperwork have been stored on the central server of the second processor-based system.

21. The method of claim 20, providing a web-based interface accessible to a user further comprising:

supplying a plurality of filters to the user of the web-based interface, the plurality of filters enabling the user to generate the patient list by entering search criteria into the web-based interface.

22. The method of claim 20, further comprising:
associating a first time with receipt of the radiographic image of the patient, the first time being associated with a first status icon;
associating a second time with receipt of the patient paperwork of the patient, the second time being associated with a second status icon; and
associating a third time with generation of the preliminary report of the patient, the third time being associated with a third status icon;
wherein the first time, second time, and third time are presented on the web-based user interface.

23. An article comprising a tangible computer-readable medium for storing instructions for enabling a processor-based system to:
retrieve a radiographic image for a patient, the radiographic image including a medical record number of the patient, wherein the radiographic image is stored on an image server of a computer processor-based system;
retrieve patient paperwork for the patient, the patient paperwork being transmitted along with the medial record number of the patient, wherein the patient paperwork is stored on a central server of the computer processor-based system;
provide a web-based interface accessible to a user, the web-based interface comprising a patient name, medical record number, and status of the patient, the status of the patient being indicated by one or more of the following status icons:
a first status icon indicating when the patient paperwork has been retrieved;
a second status icon indicating when the radiographic image has been retrieved; and
a third status icon indicating when the preliminary report has been generated;
wherein the status and associated status icon of the patient is changed when either the radiographic image or the patient paperwork are received; and
generate a preliminary report based on the radiographic image and the patient paperwork, the preliminary report comprising a first timestamp field indicating a first time of completion of the preliminary report;
review the preliminary report by a reviewing entity, the preliminary report further comprising a second timestamp field indicating a second time of review of the preliminary report; and
provide a template of the preliminary report to the web-based interface, the template including a diagnosis field, a findings field, and a scoring system, wherein the template is saved as the preliminary report of the patient once the diagnosis field and the findings field are completed, and the scoring system enables the reviewing entity to denote either textually, graphically, or both agreement or disagreement with the original generation of the preliminary report;
wherein the preliminary report is generated when the status of the patient indicates that both the radiographic image and the patient paperwork have been received by the second processor-based system.

24. The article of claim 23, further storing instructions for enabling a processor-based system to:

display a patient list in the web-based interface, the patient list comprising a subset of all patients whose radiographic images or patient paperwork have been stored in the system; and update the scoring system of the preliminary report, wherein the scoring system enables the reviewing entity to denote either textually, graphically, or both agreement or disagreement with the original generation of the preliminary report.

* * * * *